United States Patent [19]
Schmaier et al.

[11] Patent Number: 6,143,719
[45] Date of Patent: Nov. 7, 2000

[54] BRADYKININ ANALOGS AS SELECTIVE THROMBIN INHIBITORS

[75] Inventors: Alvin H. Schmaier, Ann Arbor; Ahmed A. K. Hasan, Dexter, both of Mich.

[73] Assignee: The Regents of the University of Michigan, Ann Arbor, Mich.

[21] Appl. No.: 08/676,242

[22] PCT Filed: Jun. 7, 1996

[86] PCT No.: PCT/US96/09940

§ 371 Date: Jul. 16, 1996

§ 102(e) Date: Jul. 16, 1996

[87] PCT Pub. No.: WO96/41640

PCT Pub. Date: Dec. 27, 1996

Related U.S. Application Data

[60] Provisional application No. 60/000,096, Jun. 9, 1995.

[51] Int. Cl.$^7$ ........................... A61K 38/16; C07K 14/00
[52] U.S. Cl. ........................... 514/12; 514/13; 514/14; 514/15; 514/16; 514/17; 514/18; 530/324; 530/325; 530/326; 530/327; 530/328; 530/329; 530/330
[58] Field of Search ........................ 530/314, 324, 530/325, 326, 327, 328, 329, 330; 514/12, 13, 14, 15, 16, 17, 18

[56] References Cited

U.S. PATENT DOCUMENTS

| | | | |
|---|---|---|---|
| 4,638,047 | 1/1987 | Szelke et al. | 530/332 |
| 4,693,993 | 9/1987 | Stewart et al. | 514/14 |
| 4,870,017 | 9/1989 | Ben-Bassat et al. | 204/298.12 |
| 4,923,963 | 5/1990 | Stewart et al. | 530/314 |
| 5,231,080 | 7/1993 | Scholkens | 514/2 |
| 5,300,490 | 4/1994 | Kunihiro et al. | 514/8 |
| 5,350,578 | 9/1994 | Griffin et al. | 424/94.64 |
| 5,385,889 | 1/1995 | Kyle et al. | 514/15 |
| 5,409,899 | 4/1995 | Fauchere et al. | 514/15 |
| 5,416,191 | 5/1995 | Cheronis et al. | 530/314 |
| 5,446,131 | 8/1995 | Maraganore | 530/326 |
| 5,472,945 | 12/1995 | Schmaier et al. | 514/12 |

FOREIGN PATENT DOCUMENTS

| | | |
|---|---|---|
| WO 92/17201 | 10/1991 | WIPO . |
| WO 94/11021 | 5/1994 | WIPO . |

OTHER PUBLICATIONS

Stewart et al., "Bradykinin Chemistry: Agonists and Antagonists", *Advance in Experimental Medicine and Biology*. New York: Plenum Press, 1983, p. 585–589, especially p. 588.
Martin et al., "Bradykinin Stimulates Phosphodiesteratic Cleavage of Phosphatidylcholine in Cultured Endothelial Cells", *Biochemical and Biophysical Research Communication*. Dec. 30, 1988, vol. 157, No. 3, pp. 1271–1279.
Chem. abstr., vol. 107, No. 17, Oct. 26, 1987 (Columbus. Ohio, USA), p. 146, col. 2, the abstract No. 148141v, Alheid et al., "Endothelium–derived relaxing factor from cultured human endothelial cells inhibits aggregation of human platelets", *Thromb. Res.* 1987, 47(5), 561–71.
Chem. abstr., vol. 84, No. 21, May 24, 1976 (Columbus. OH, USA), p. 417, col. 2, the abstract No. 148985e, Shikawa et al., "Prostaglandin synthetase activity and hormone responsiveness in normal and SV40 transformed WI–38 fibroblasts", *J. of Cyclic Nucleotide Res.* 1976, 2(2), 115–28.
Database CAplus on STN, Chemical Abstracts Service, (Columbus, OH< USA), CAplus No. 1996:519830, Hasan et al., "Bradykinin and its metabolite, Arg–Pro–Pro–Gly–Phe, are selective inhibitors of alpha–thrombin–induced platelet activation", abstract Circulation 1996.
Chem. abstr., vol. 111, No. 9, Aug. 28, 1989 (Columbus. OH, USA), p. 178, col. 2, the abstract No. 71858g, Loeb et al., "Endotherlium–dependent potentiation of human platelet aggregation", *Thromb. Res.* 1989, 54(5), 477–86.
Chem. abstr., vol. 93, No. 25, Dec. 22, 1980 (Columbus. OH, USA), p. 100, col. 1, the abstract No. 231243t, Imai et al., "Effects of prostacyclin on platelet aggregation as studied with 'filter–loop' technique in the flowing blood of the dog", *Artery*, 1980, 8(1), 90–5.
Chem. abst., vol. 107, No. 17, p. 146, col. 2, the abstract No. 148141v, Alheid et al., 'Endthelium–derived relaxing factor from cultured human endothelial cells inhibits aggregation of human platelets.' Thrmb. Res. 1987, 47(5)), 561–71, Oct. 26, 1987.
Stewart et al., 'Bradykinin Chemistry: Agonists and Antagonists'. In: Advanced in Experimental Medicine and Biology. New York: Plenum Press, 1983, p. 585–589.
Park et al., 'Synthesis of Peptides by the Solid Phase Method. III. Bradykinin: Fragments and Analogs', Can. J. Biochem. vol. 56, pp. 92–100, 1978.
Ngo et al. 'Computational Complexity Protein Structure Prediction, and the Levinthal Paradox', The Protein Folding Problem and Tertiary Structure Prediction, pp. 491–495, 1994.
J.A. Parsons, "Peptide Hormones" University Park Press, 1976, pp. 1–7.
Imai et al. Effects of Prostacyclin on Platelet Aggregation as Studied with "Filter–Loop" Technique in the Flowying Blood of the Dog, Artery, vol. 8, No. 1, pp. 63–72, 1980.
Database CAPLUS on STN, Chemical Abstracts Service, (Columbus, OH–USA), CAPLUS No. 1996:519830, Hasan et al., 'Bradykinin and its Metabolite, Arg–Pro–Pro––Gly–Phe, are Selective Inhibitors of Alpha–Thrombin–Induced Platelet Activation', abstract circulatio, 1996.

(List continued on next page.)

*Primary Examiner*—Christopher S. F. Low
*Assistant Examiner*—Anish Gupta
*Attorney, Agent, or Firm*—Seidel, Gonda, Lavorgna & Monaco, PC

[57] ABSTRACT

Thrombin-induced and ADP-induced platelet and other cell activation is inhibited without affecting thrombin's other proteolytic activity by administration of a bradykinin sequence related analogous peptide. Bradykinin analogs are peptides to which substitutions, additions or deletions have been made to the first four amino acids of the amino acid sequence of native bradykinin. The bradykinin analogs described inhibit α-thrombin-induced and ADP-induced platelet activation and secretion, inhibit α-thrombin-induced calcium mobilization, and prevent α-thrombin from cleaving its platelet receptor. The bradykinin analogs may comprise single- or multiple-chain peptides.

33 Claims, 15 Drawing Sheets

OTHER PUBLICATIONS

Martin et al., 'Bradykinin Stimulates Phophodiesteratic Cleavage of Phosphatidylcholine in Cultured Endothelial Cells', Biochemical and Biophysical Research Communication. Dec. 30, 1988, vol. 157, No. 3, p. 1271–1279.

Hasan et al., 'The Carboxyl Terminus of Bradykinin and Amino Terminus of Light Chain of Kininogens Comprise an Endothelial Cell Binding Domain' Journal of Biological Chemistry, vo. 269, No. 50, Dec. 1994.

J.A Parsons, 'Peptide Hormones', published 1976 by University Park Press (Baltimore), pp. 1–7.

Hasan, et al., "The Carboxyl Terminus of Bradykinin and Amino Terminus of the Light Chain of Kininogens Comprise and Endothelial Cell Binding Domain", *The Journal of Biological Chemistry,* (Dec. 16, 1994), vol. 269, No. 50, pp. 31822–31830.

Wirth, et al., "Hoe 140 a new potent and long acting bradykinin–antagonist: in vivo studies", *British Journal of Pharmacology,* (Mar., 1991), vol. 102, No. 3, pp. 774–777.

Vu, et al., "Molecular Cloning of a Functional Thrombin Receptor Reveals a Novel Proteolytic Mechanism of Receptor Activation", *Cell,* (Mar. 22, 1991), vol. 64, pp. 1057–1068.

Puri, et al., "Inhibition Of Thrombin–Induced Platelet Aggregation By High Molecular Weight Kininogen", *Transactions of the Association of American Physicians,* (1987), vol. C, pp. 232–240.

Puri, et al., "Cleavage Of A 100 kDa Membrane Protein (Aggregin) During Thrombin–Induced Platelet Aggregation Is Mediated By The High Affinity Thrombin Receptors", *Biochemical and Biophysical Research Communications,* (Aug. 15, 1989), vol. 162, No. 3, pp. 1017–1024.

Puri, et al., "Reocclusion after thrombolytic therapy: strategies for inhibiting thrombin–induced platelet aggregation", *Blood Coagulation and Fibrinolysis,* (1993) vol. 4, pp. 465–478.

Puri, et al., "High Molecular Weight Kininogen Inhibits Thrombin–Induced Platelet Aggregation and Cleavage of Aggregin by Inhibiting Binding of Thrombin to Platelets", *Blood,* (Feb. 1, 1991), vol. 77, No. 3, pp. 500–507.

Meloni, et al., "Low Molecular Weight Kininogen Binds to Platelets to Modulate Thrombin–induced Platelet Activation", *The Journal of Biological Chemistry,* (Apr. 13, 1991), vol. 265, No. 11, pp. 6786–6794.

Hasan, et al., "Bradykinin And Related Peptides Selectively Inhibit α–Thrombin's Ability To Activate The Platelet Thrombin Receptor", *Thrombosis and Haemostasis,* (Jun., 1995), vol. 73, No. 6, p. 94 (Abstract).

Imai and Matsubara, *Artery* 8(1) :63–72 (1980).

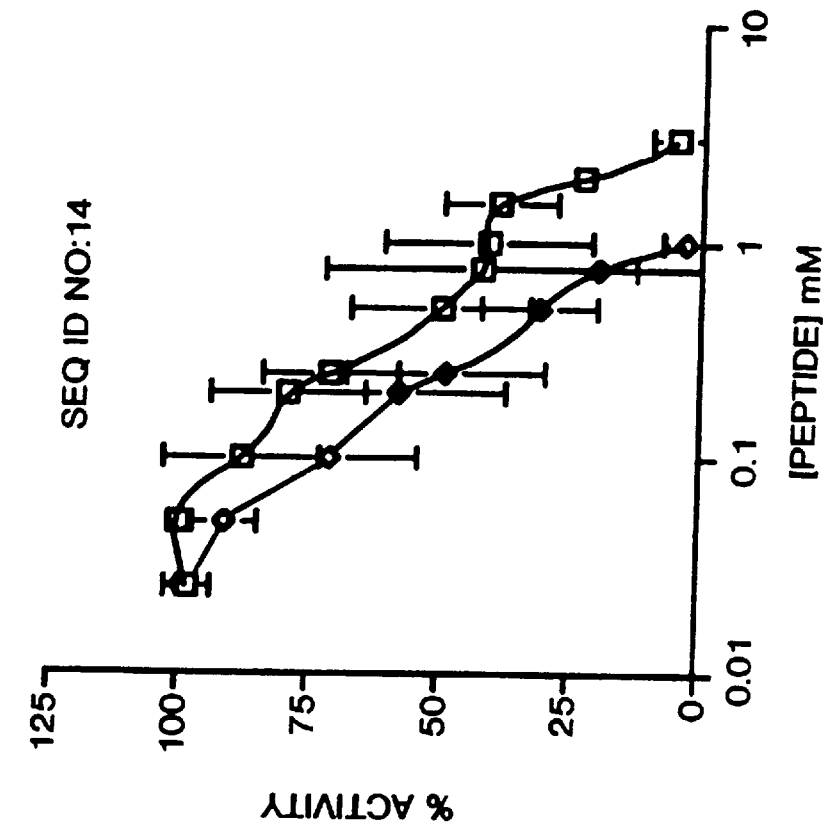
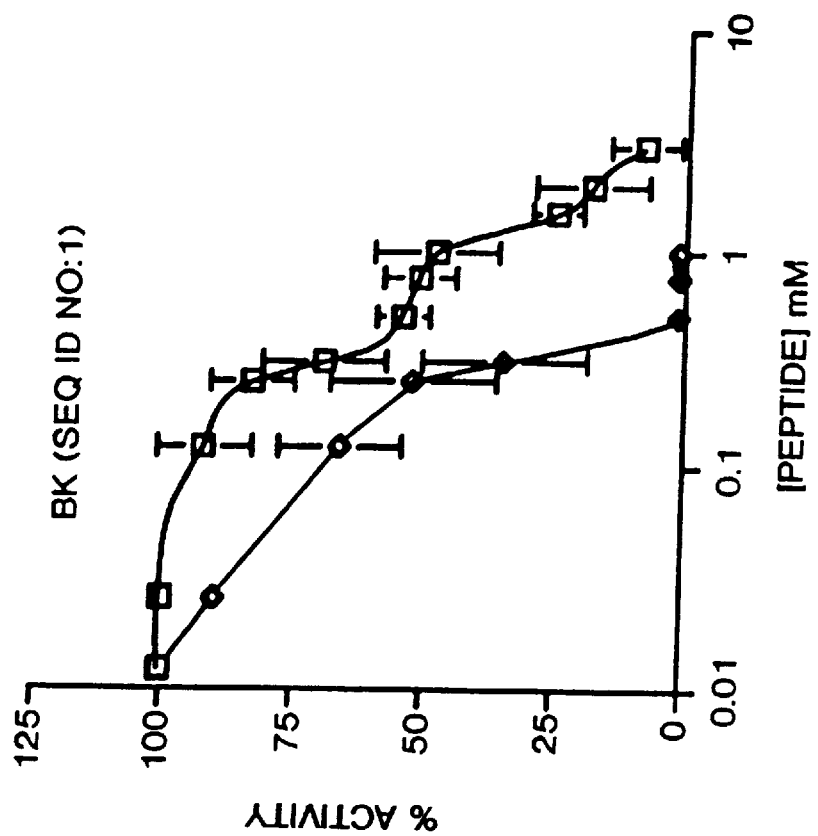
FIG. 1A
FIG. 1B

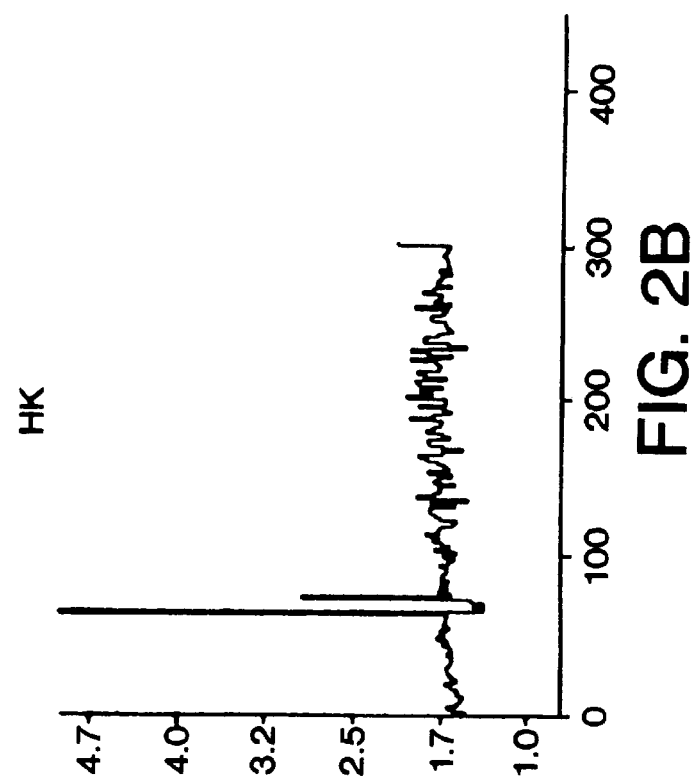
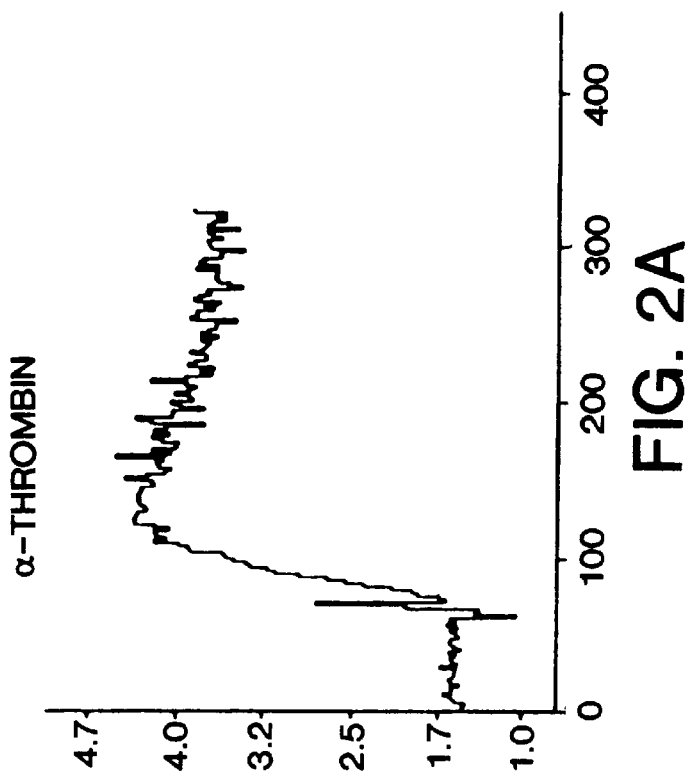

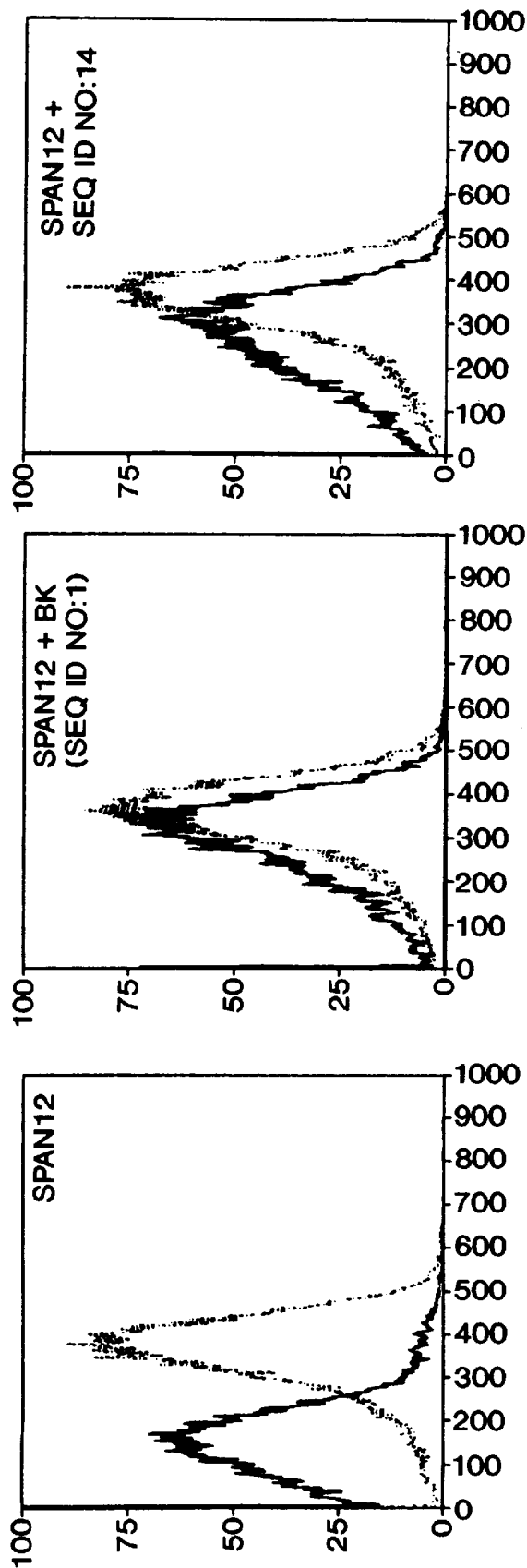

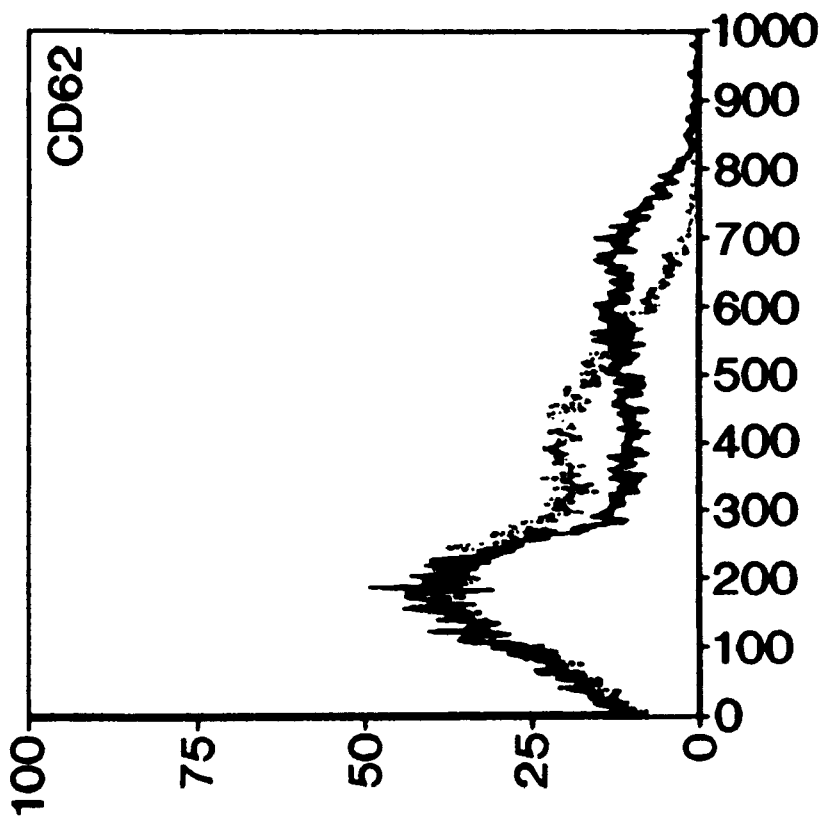
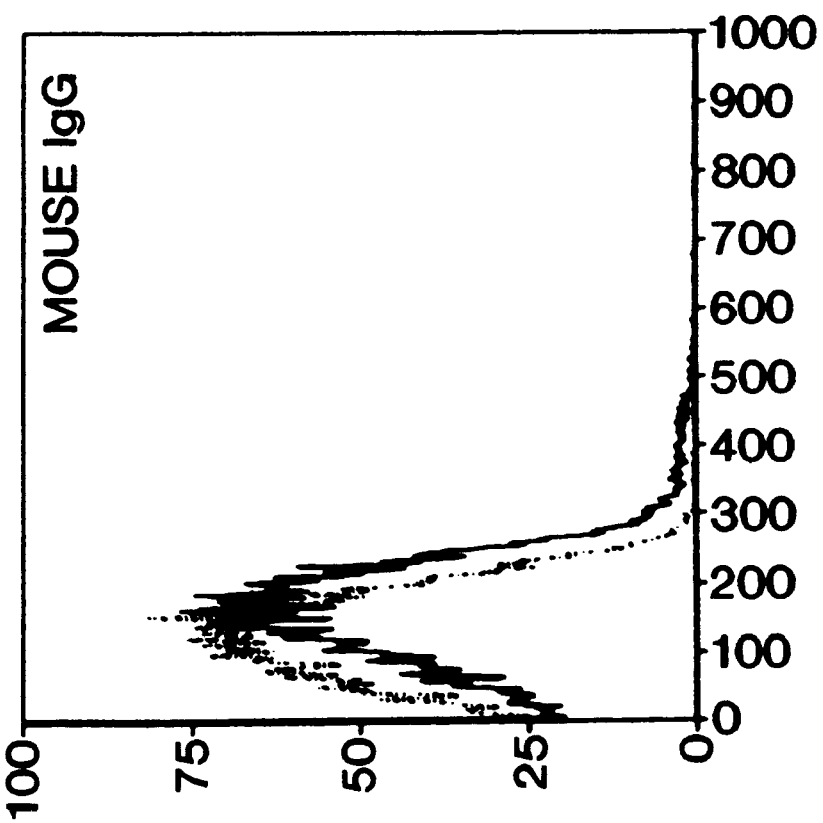
FIG. 7D
FIG. 7C

SEQUENCE LISTING

```
<160> NUMBER OF SEQ ID NOS: 24

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence: Bradykinin

<400> SEQUENCE: 1

Arg Pro Pro Gly Phe Ser Pro Phe Arg
  1               5

<210> SEQ ID NO 2
<211> LENGTH: 12
<212> TYPE: PRT
<213> ORGANISM: Artificial Sequence
<220> FEATURE:
<223> OTHER INFORMATION: Description of Artificial Sequence: Peptide
      NAT-12, which spans alpha-thrombin cleavage cite
      on thrombin receptor

<400> SEQUENCE: 2

Asn Ala Thr Leu Asp Pro Arg Ser Phe Leu Leu Arg
  1               5                  10

<210> SEQ ID NO 3
<211> LENGTH: 9
```

```
<212> TYPE: PRT
<213> ORGANISM: Artificial Sequence
<220> FEATURE:
<223> OTHER INFORMATION: Description of Artificial Sequence: Epitope on
      thrombin receptor

<400> SEQUENCE: 3

Asn Pro Asn Asp Lys Tyr Glu Pro Phe
  1               5

<210> SEQ ID NO 4
<211> LENGTH: 15
<212> TYPE: PRT
<213> ORGANISM: Artificial Sequence
<220> FEATURE:
<223> OTHER INFORMATION: Description of Artificial Sequence: Control
      peptide

<400> SEQUENCE: 4

Phe Asn Gln Thr Gln Pro Glu Arg Gly Asp Asn Asn Leu Thr Arg
  1               5                  10                  15

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: Bradykinin
      analog

<400> SEQUENCE: 5

Phe Pro Arg Pro Gly
  1               5

<210> SEQ ID NO 6
<211> LENGTH: 16
<212> TYPE: PRT
<213> ORGANISM: Artificial Sequence
<220> FEATURE:
<223> OTHER INFORMATION: Description of Artificial Sequence: Scrambled
      peptide

<400> SEQUENCE: 6

Phe Ser Gly Pro Lys Arg Ser Pro Ile Met Gly Arg Pro Ser Phe Arg
  1               5                  10                  15

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Bradykinin
      analog

<400> SEQUENCE: 7

Phe Ser Pro Phe Arg Ser Ser
  1               5

<210> SEQ ID NO 8
<211> LENGTH: 11
<212> TYPE: PRT
<213> ORGANISM: Artificial Sequence
<220> FEATURE:
<223> OTHER INFORMATION: Description of Artificial Sequence: Bradykinin
      analog

<400> SEQUENCE: 8

Gly Phe Ser Pro Phe Arg Ser Ser Arg Ile Gly
```

-continued

```
                1               5                  10

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence: Scrambled
      peptide

<400> SEQUENCE: 9

Gly Pro Phe Pro Arg
  1               5

<210> SEQ ID NO 10
<211> LENGTH: 11
<212> TYPE: PRT
<213> ORGANISM: Artificial Sequence
<220> FEATURE:
<223> OTHER INFORMATION: Description of Artificial Sequence: Bradykinin
      analog

<400> SEQUENCE: 10

Lys Ile Cys Val Gly Cys Pro Arg Asp Ile Pro
  1               5                  10

<210> SEQ ID NO 11
<211> LENGTH: 27
<212> TYPE: PRT
<213> ORGANISM: Artificial Sequence
<220> FEATURE:
<223> OTHER INFORMATION: Description of Artificial Sequence: Bradykinin
      analog

<400> SEQUENCE: 11

Leu Asp Cys Asn Ala Glu Val Tyr Val Val Pro Trp Glu Lys Lys Ile
  1               5                  10                  15

Tyr Pro Thr Val Asn Cys Gln Pro Leu Gly Met
             20                  25

<210> SEQ ID NO 12
<211> LENGTH: 16
<212> TYPE: PRT
<213> ORGANISM: Artificial Sequence
<220> FEATURE:
<223> OTHER INFORMATION: Description of Artificial Sequence: Bradykinin
      analog

<400> SEQUENCE: 12

Met Ile Ser Leu Met Lys Arg Pro Pro Gly Phe Ser Pro Phe Arg Ser
  1               5                  10                  15

<210> SEQ ID NO 13
<211> LENGTH: 13
<212> TYPE: PRT
<213> ORGANISM: Artificial Sequence
<220> FEATURE:
<223> OTHER INFORMATION: Description of Artificial Sequence: Bradykinin
      analog

<400> SEQUENCE: 13

Met Lys Arg Pro Pro Gly Phe Ser Pro Phe Arg Ser Ser
  1               5                  10

<210> SEQ ID NO 14
<211> LENGTH: 16
<212> TYPE: PRT
```

```
<213> ORGANISM: Artificial Sequence
<220> FEATURE:
<223> OTHER INFORMATION: Description of Artificial Sequence: Bradykinin
      analog

<400> SEQUENCE: 14

Met Lys Arg Pro Pro Gly Phe Ser Pro Phe Arg Ser Ser Arg Ile Gly
  1               5                  10                  15

<210> SEQ ID NO 15
<211> LENGTH: 26
<212> TYPE: PRT
<213> ORGANISM: Artificial Sequence
<220> FEATURE:
<223> OTHER INFORMATION: Description of Artificial Sequence: Bradykinin
      analog

<400> SEQUENCE: 15

Asn Ala Thr Phe Tyr Phe Lys Ile Asp Asn Val Lys Lys Ala Arg Val
  1               5                  10                  15

Gln Val Val Ala Gly Lys Lys Tyr Phe Ile
              20                  25

<210> SEQ ID NO 16
<211> LENGTH: 6
<212> TYPE: PRT
<213> ORGANISM: Artificial Sequence
<220> FEATURE:
<223> OTHER INFORMATION: Description of Artificial Sequence: Bradykinin
      analog

<400> SEQUENCE: 16

Pro Pro Gly Phe Ser Pro
  1               5

<210> SEQ ID NO 17
<211> LENGTH: 16
<212> TYPE: PRT
<213> ORGANISM: Artificial Sequence
<220> FEATURE:
<223> OTHER INFORMATION: Description of Artificial Sequence: Bradykinin
      analog

<400> SEQUENCE: 17

Ser Pro Phe Arg Ser Ser Arg Ile Gly Glu Ile Lys Glu Glu Thr Thr
  1               5                  10                  15

<210> SEQ ID NO 18
<211> LENGTH: 6
<212> TYPE: PRT
<213> ORGANISM: Artificial Sequence
<220> FEATURE:
<223> OTHER INFORMATION: Description of Artificial Sequence: Thrombin
      receptor activation peptide

<400> SEQUENCE: 18

Ser Phe Leu Leu Arg Asn
  1               5

<210> SEQ ID NO 19
<211> LENGTH: 5
<212> TYPE: PRT
<213> ORGANISM: Artificial Sequence
<220> FEATURE:
<223> OTHER INFORMATION: Description of Artificial Sequence: Bradykinin
      analog

<400> SEQUENCE: 19
```

Arg Pro Pro Gly Phe
1               5

<210> SEQ ID NO 20
<211> LENGTH: 4
<212> TYPE: PRT
<213> ORGANISM: Artificial Sequence
<220> FEATURE:
<223> OTHER INFORMATION: Description of Artificial Sequence: Bradykinin
      analog

<400> SEQUENCE: 20

Arg Pro Pro Gly
1

<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence:
      Non-bradykinin analog derived from kininogen domain 3

<400> SEQUENCE: 21

Leu Asn Ala Glu Asn Asn Ala
1               5

<210> SEQ ID NO 22
<211> LENGTH: 64
<212> TYPE: PRT
<213> ORGANISM: Artificial Sequence
<220> FEATURE:
<223> OTHER INFORMATION: Description of Artificial Sequence: From human
      kininogen heavy chain

<400> SEQUENCE: 22

Cys Asn Ala Glu Val Tyr Val Val Pro Trp Glu Lys Lys Ile Tyr Pro
1               5                   10                  15

Thr Val Asn Cys Gln Pro Leu Gly Met Ile Ser Leu Met Lys Arg Pro
            20                  25                  30

Pro Gly Phe Ser Pro Phe Arg Ser Ser Arg Ile Gly Glu Ile Lys Glu
        35                  40                  45

Glu Thr Thr Val Ser Pro Pro His Thr Ser Met Ala Pro Ala Gln Asp
    50                  55                  60

<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence: From human
      kininogen heavy chain

<400> SEQUENCE: 23

Gly Met Ile Ser Leu Met Lys
1               5

<210> SEQ ID NO 24
<211> LENGTH: 9
<212> TYPE: PRT
<213> ORGANISM: Artificial Sequence
<220> FEATURE:

-continued

<223> OTHER INFORMATION: Description of Artificial Sequence: From human
    kininogen heavy chain

<400> SEQUENCE: 24

Phe Ser Pro Phe Arg Ser Ser Arg Ile
 1               5

BRADYKININ ANALOGS AS SELECTIVE THROMBIN INHIBITORS

CROSS-REFERENCE TO RELATED APPLICATIONS

This application claims priority from U.S. provisional patent application No. 60/000,096 filed Jun. 9, 1995.

REFERENCE TO GOVERNMENT GRANT

The invention described herein was made, in part, in the course of work supported by the National Heart Lung and Blood Institute under Grant No. L-35553. The government has certain rights in the invention.

FIELD OF THE INVENTION

This invention relates to the inhibition of α-thrombin-induced and ADP-induced cell activation.

BACKGROUND OF THE INVENTION

Bradykinin is a vasoactive peptide released from the precursor plasma kininogens by kallikrein and other enzymes (Silva et al., *Amer. J. Physiol.* 156: 261–274 (1949)). Bradykinin has been described to have multiple physiologic functions, including the stimulation of prostacyclin production (Hong, S. L., *Thromb. Res.* 18, 787 (1980); Crutchley et al., *Biochim Biophy Acta* 751, 99 (1983)) and the stimulation of the release of plasminogen activators (Smith et al., *Blood* 66, 835 (1983)). Bradykinin induces superoxide formation and endothelium-dependent smooth muscle hyperpolarization (Holland, J. A. et al., *J. Cell Physiol.* 143, 21 (1990); Nakashima, M. et al., *J. Clin. Invest.* 92, 2867 (1993)). Along with acetylcholine, bradykinin is the major inducer of nitric oxide formation (Palmer, R. M. J. et al., *Nature* 327, 524 (1987)). Bradykinin has been characterized to produce vasodilation in most vascular beds which in the coronary artery circulation results in increased blood flow (Line et al., *J. Mol. Cell Cardiol.* 24, 909 (1992)). These latter features have led some to characterize bradykinin as a cardioprotective agent (Line et al., supra; Gohlke et al., *Hypertension* 23, 411 (1994); Parratt et al., *Cardiovascular Research* 28, 183 (1994); Zanzinger et al., *Cardiovascular Research* 28, 209 (1994)). Bradykinin's elevation by angiotensin converting enzyme inhibitors is believed to be the mechanism by which these drugs promote their beneficial effects on heart failure.

In addition to the delivery of bradykinin, its parent proteins, high (HK) and low (LK) molecular weight kininogens, also have the ability to be selective inhibitors of α-thrombin, inhibiting α-thrombin's ability to activate cells without interfering with its enzymatic ability (Meloni et al., *J. Biol. Chem.* 266, 6786 (1991); Puri et al., *Blood* 77, 500 (1991)). This activity was believed to be a unique function for the kininogens; one which had not been ascribed to other proteins. Most naturally occurring human protein inhibitors of α-thrombin are directed towards its protease activity. HK and LK are selective inhibitors of thrombin's ability to activate platelets by blocking α-thrombin from binding to the platelet membrane (Meloni et al., supra; Puri et al., supra). This activity of the kininogens appeared to be localized to domain 3 on their heavy chain since isolated domain 3 retains that activity (Jiang et al., *J Biol. Chem.* 267, 3712 (1992)).

Inhibition of platelet activation by domain 3 is observed by a marked decrease in the platelet's ability to aggregate and secrete their granule contents. The granule contents comprise proteins which participate in hemostasis, thrombosis, and the inflammatory response. Inhibition of endothelial cell activation may similarly be observed by a decrease in secretion of endothelial cell contents such as tissue plasminogen activator and von Willebrand factor.

The domain 3 polypeptide like its parent proteins HK and LK functions to inhibit cell activation by blocking thrombin binding to its target cells. This polypeptide is a selective inhibitor of thrombin-induced platelet activation. Administration of domain 3 therefore does not impact on induction of platelet activation by physiological substances other than thrombin, such as, for example collagen, adenosine diphosphate, epinephrine and platelet activating factor.

Interventional procedures for coronary artery disease such as coronary thrombolysis or percutaneous transluminal coronary angioplasty have made good efforts in reducing mortality from acute coronary thrombosis. However, after intracoronary thrombolysis with lytic agents, the reocclusion rate is high. The major cause for reocclusion is platelet thrombus. When artificial dacron grafts are anastomosed to human arteries, up to 30% of all patients will develop a platelet thrombosis within hours of surgery. This expected high complication rate frequently requires an additional operation with attendant complications. Thus, additional therapies are needed to prevent these reocclusion events due to platelet thrombi.

Two competing classes of antiplatelet agents for the prevention of coronary thrombosis are being considered. One class of agents, including monoclonal antibody 7E3, aims to block the final common pathway of platelet activation by inhibiting glycoprotein IIbIIIa (GPIIb/IIIa), integrin $\alpha_{IIb}\beta_3$. 7E3 is an effective agent, but it is a murine antibody and is antigenic in humans. A second class of antiplatelet agents inhibit a presumed, primary initiating agent of platelet activation, α-thrombin. Infusions of Phe-Pro-Arg-chloromethylketone (PPACK), a potent inhibitor of α-thrombin's proteolytic activity, prolongs the bleeding time, a crude measure of platelet function (Hanson, S. R. et al., *Proc. Natl. Acad. Sci.* 85, 3184–3188 (1988)). The first generation of potent α-thrombin proteolytic inhibitors to enter into clinical trials is a recombinant product derived from medicinal leeches, hirudin. This compound, which is a small molecular mass and is not considered to be antigenic, is a potent anti-thrombin. A synthetic analog of hirudin, hirulog, combines the anion exosite I binding properties of hirudin with the proteolytic inhibitory activity of PPACK. In Phase III clinical trials, both drugs were effective inhibitors of platelet activation; however, the tradeoff for effective anticoagulation was increased hemorrhage leading to the termination of three clinical trials. Thus non-selective proteolytic inhibitors of α-thrombin are not clinically tolerated and may never have commercial significance.

An ideal anti-thrombotic to prevent arterial thrombosis would be one which prevents platelet and endothelial cell activation without preventing the proteolytic activity of α-thrombin to clot fibrinogen and activate protein C, factor XIII, and factors V and VIII. Only two known proteins, high molecular weight (HK) and low molecular weight (LK) kininogens, are naturally occurring selective anti-thrombins (Meloni, F. J. et al., *J. Biol. Chem.* 266; 6786–6794 (1991); Puri, R. N. et al., *Blood* 77:500–507 (1991)). Both low and high molecular weight kininogens have identical amino acid sequences from their amino-terminus through 12 amino acids beyond the carboxy-terminus of bradykinin. LK and HK share a common heavy chain (62 kDa), the bradykinin (BK) moiety (0.9 kDa), and the first 12 amino acids of the amino terminal portion of each of their "light chains"

(Takagaki, Y. et al., *J. Biol. Chem.* 260:8601–8609 (1985); Kitamura, N. et al., *J. Biol. Chem.*, 260:8610–8617 (1985)). This identity corresponds to residues 1 through about residue 383. See Salveson et al., *Biochem J.* 234, 429 (1986); Kellerman et al., *Eur. J. Biochem.* 154, 471 (1986). They diverge in the size of their light chains; the light chain of LK is 4 kDa; that of HK is 56 kDa. Takagaki et al., supra; Kitamura et al., supra.

Hereinafter, "human kininogen" shall mean, unless otherwise indicated, both high and low molecular weight forms of any kininogen molecule, in all its various forms derived from human plasma, platelets, endothelial cells, granulocytes, or skin or other tissues or organs, regardless of whether it is found in the fluid or the tissue phase.

"Light chain" shall mean, when referring or relating to human kininogen, the 56 kDa intermediate plasma kallikrein-cleavage fragment of HK which has the ability to correct the coagulant defect in total kininogen-deficient plasma.

"Heavy chain" shall mean, when referring or relating to human kininogen, the 64 kDa kallikrein-cleavage fragment of HK or LK, which is free of bradykinin and "light chain".

"Domain 3" with respect to the kininogen heavy chain shall mean the trypsin-cleavage fragment of the human kininogen heavy chain which is about 21 kDa.

By "natural amino acid" is meant any of the twenty primary, naturally occurring amino acids which typically form peptides and polypeptides. By "synthetic amino acid" is meant any other amino acid, regardless of whether it is prepared synthetically or derived from a natural source.

By "BK analog" is meant a peptide having an amino acid sequence analogous to the sequence of the nonapeptide bradykinin, which is capable of inhibiting α-thrombin from cleaving its receptor on platelets and other cells, such that the peptide prevents the alteration or loss of the SPAN12 epitope on the thrombin receptor, and blocks cleavage of a peptide, NAT12 (SEQ ID NO:2), which spans the α-thrombin cleavage site on the thrombin receptor. BK analogs are thus able to inhibit thrombin-induced platelet activation.

Some of the nomenclature of the subject matter of the present invention involves lengthy terms. It is customary for those skilled in the art to abbreviate these terms in a manner well-known to the art. These general and customary abbreviations are set forth below and may be utilized in the text of this specification.

Abbreviations

ATAP138 monoclonal antibody specific for an epitope on the thrombin receptor, which epitope is preserved following α-thrombin cleavage of the receptor
BK: bradykinin
D3: domain 3 of kininogen
DFP: diisopropyl fluorophosphate
D-Tic: D-1,2,3,4-tetrahydroisoquinolin-3-yl-carbonyl
EDTA: ethylenediaminetetraacetic acid
FITC: fluorescein isothiocyanate
HBTU: 2-(1-H-benzotriazole-1-YL)-1,1,3,3-tetramethyl-uroniumhexofluorophosphate
HOBt 1-hydroxybenzotriazole
HK: human high molecular weight kininogen
4Hyp: (4R)-4-hydroxypropyl
LK: human low molecular weight kininogen
NAT12: peptide sequence Asn-Ala-Thr-Leu-Asp-Pro-Arg-Ser-Phe-Leu-Leu-Arg, which spans the α-thrombin cleavage site on the thrombin receptor
Oic: (3a5, 7a5)-octahydroindol-2-yl-carbonyl
PADGEM: platelet activation dependent granule external membrane protein, also known as P-selectin, GMP140 or CD62
PGE1: prostaglandin E1
PMSF: phenylmethylsulfonylfluoride
SDS-PAGE: sodium dodecylsulfate polyacrylamide gel electrophoresis
SPAN12 monoclonal antibody specific for the sequence Asn-Ala-Thr-Leu-Asp-Pro-Arg-Ser-Phe-Leu-Leu-Arg (SEQ ID NO:2) which spans the α-thrombin cleavage site on the thrombin receptor
Thi: 3-(2-thienyl)alanyl
TRAP: thrombin receptor activation peptide, which has the amino acid sequence Ser-Phe-Leu-Leu-Arg-Asn (SEQ ID NO: 18)
Tris: tris(hydroxymethyl)aminomethane

SUMMARY OF THE INVENTION

The invention comprises a method of inhibiting thrombin-induced platelet or other cell activation comprising administering to an individual in need of such treatment an effective amount of a peptide which inhibits thrombin activation of platelets or other cells, wherein said peptide has an amino acid sequence of the formula:

$$X_1\text{-Arg-Pro-Pro-Gly-}X_2 \qquad (I)$$

wherein:
$X_1$ is from zero to thirty natural or synthetic amino acids; and
$X_2$ is from zero to thirty natural or synthetic amino acids; provided that the peptide may not be native bradykinin.

In one embodiment of the invention, $X_1$ is zero to seven amino acids and $X_2$ is zero to nine amino acids. In a preferred embodiment of the invention, the peptide according to formula I has the sequence Arg-Pro-Pro-Gly-Phe (SEQ ID NO:19).

The invention further comprises a method for inhibiting ADP-induced platelet activation, which method comprises administering to an individual in need of such treatment an effective amount of a peptide according to formula I.

Another embodiment of the invention comprises a method for preventing platelet aggregation comprising administering to an individual in need of such treatment an effective amount of a peptide according to formula I.

According to yet another embodiment of the invention, a method of inhibiting ADP-induced platelet activation comprises administering to an individual in need of such treatment an effective amount of a peptide, which inhibits thrombin activation of platelets or other cells, wherein said peptide is comprised of one or more segments having the amino acid sequence $X_1$-Arg-Pro-Pro-Gly-$X_2$ and the peptide has the formula:

$$L\text{-}(X_1\text{-Arg-Pro-Pro-Gly-}X_2) \qquad (II)$$

wherein:
L is a linker comprising a covalent bond or chemical group;
$X_1$, which may be the same or different in each segment, is from zero to thirty natural or synthetic amino acids;
$X_2$, which may be the same or different in each segment, is from zero to thirty natural or synthetic amino acids; and
n is an integer from two to twenty.

In one embodiment of the invention, the segment of a peptide according to formula II has the sequence Arg-Pro-Pro-Gly-Phe (SEQ ID NO:19).

The invention further comprises a method for inhibiting ADP-induced platelet activation, which method comprises administering to an individual in need of such treatment an effective amount of a peptide according to formula II, wherein L, $X_1$, $X_2$, and n are defined as above.

Another embodiment of the invention comprises a method for preventing platelet aggregation comprising administering to an individual in need of such treatment an effective amount of a peptide according to formula II, wherein L, $X_1$, $X_2$, and n are defined as above.

The invention as described herein also comprises a compound having the formula:

Arg-Pro-Pro-Gly-Phe-Glu

Lys-Arg-Pro-Pro-Gly-Phe

A further embodiment of the invention comprises a compound having the formula:

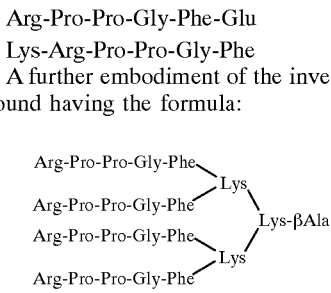

DESCRIPTION OF THE FIGURES

FIGS. 1A–1D are plots of the inhibition of α-thrombin-induced platelet aggregation and secretion by BK (1A) and BK analogs (1B: SEQ ID NO:14, IC: SEQ ID NO:13; ID: SEQ ID NO:17), incubated in the absence or presence of increasing concentrations of peptides before the addition of human α-thrombin to start the reaction: % residual aggregation activity (◇); % residual [$^{14}$C]5-hydroxytryptamine secretion (□). Each figure is the mean ±SEM of the data derived from at least three experiments.

FIGS. 2A–2D are plots of α-thrombin-induced calcium mobilization in human platelets in the presence of α-thrombin alone (2A), HK (2B); BK (SEQ ID NO:1) (2C); or BK analog SEQ ID NO: 14 (2D). Each figure is a representative experiment from at least three experiments.

FIGS. 6A–6F are flow cytograms showing the effect of various BK analogs on expression of the antigenicity of the thrombin receptor. Washed platelets were incubated with monoclonal antibody SPAN12 alone (FIG. 6A) or in the presence of 1 mM of BK (FIG. 6B), SEQ ID NO:14 (FIG. 6C), SEQ ID NO: 17 (FIG. 6D) or SEQ ID NO:4 (FIG. 6E). The ghost curves represent unstimulated platelets; the solid curves represent α-thrombin activated platelets. Mouse IgG (FIG. 6F) was used as a control. Each figure is a representative experiment of three experiments.

FIGS. 7A–7D are flow cytograms showing the influence of BK analog SEQ ID NO:14 on the binding of monoclonal antibody ATAP138 to the thrombin receptor after α-thrombin activation of platelets (FIG. 7B). Control experiments were also performed with mouse IgG (FIG. 7C) and an antibody to CD62 (FIG. 7D). The ghost curves represent thrombin receptor expression by unstimulated platelets; the solid curves represent expression by α-thrombin activated platelets. The flow cytograms of FIGS. 7A–7D were performed on the same day with the same platelets as the flow cytograms in FIGS. 6A–6D. Each figure is a representative experiment of three experiments.

FIG. 8E is the chromatograph for NAT12 (SEQ ID NO:2) incubated with HK in the presence of α-thrombin, while FIG. 8F is the corresponding chromatograph for a non-BK analog peptide (SEQ ID NO:21).

FIG. 1 is an aggregometer tracing of γ-thrombin-induced (20 nM) aggregation of human platelets treated in the presence of 1 mM of a non-BK analog peptide (SEQ ID NO:21), 0.5 mM of a BK analog heterodimer ("HETERODIMER") (SEQ ID NO:21), 0.5 mM of 4-MAP, and 1 mM of a BK analog SEQ ID NO:19, and γ-thrombin alone (control).

DETAILED DESCRIPTION OF THE INVENTION

Figure 1D:
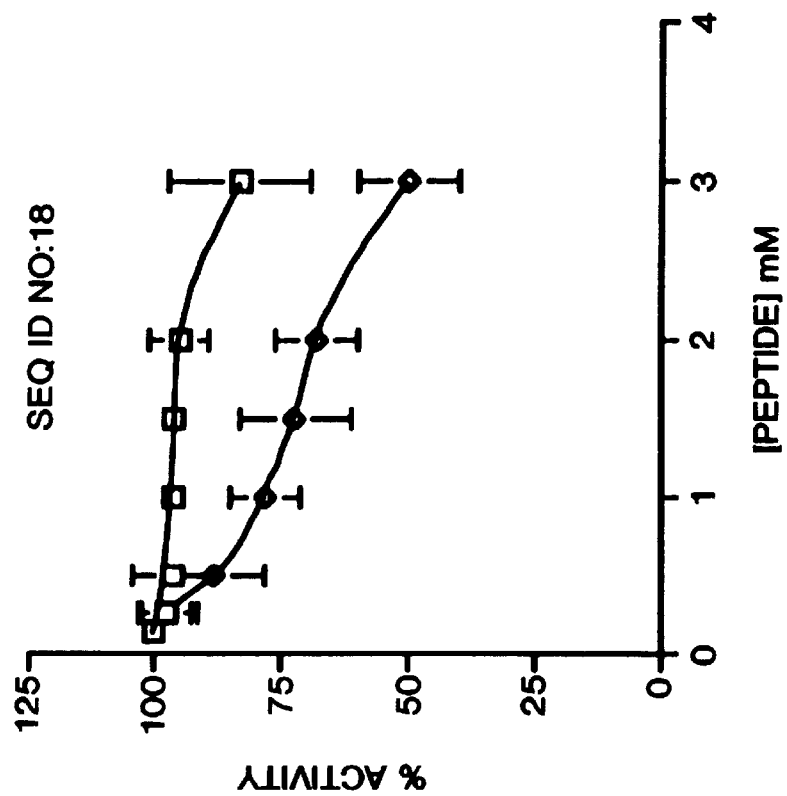

The invention is directed to a method for preventing thrombosis by the use of bradykinin sequence-related analogous peptides that act as selective anti-thrombins. The BK analogs are selective anti-thrombins because they are able to inhibit human α-thrombin and γ-thrombin from activating platelets without interfering with α-thrombin's ability to proteolyze its various substrates, e.g., fibrinogen and factor V. Most known thrombin inhibitors, hirudin, hirulog and PPACK, interfere with α-thrombin's action by blocking all of its proteolytic activity. Use of these proteolytic inhibitors to inhibit α-thrombin activation of platelets may result in excessive anticoagulation and hemorrhage. The BK analogs utilized in the present method would allow for inhibition of cell-induced plug formation without interfering with α-thrombin's enzymatic activity. BK analogs may be used to prevent arterial occlusions arising from coronary thrombosis and stroke.

We have found that the BK analogs inhibit thrombin from cleaving the thrombin receptor which is expressed on platelets. Thus, we have found that the BK analogs have the ability to inhibit thrombin-induced platelet activation by blocking cleavage of the thrombin receptor and subsequent activation of platelets by exposure of the new amino terminus of the cleaved receptor. Administration of a BK analog as described herein comprises a therapeutic method for inhibiting thrombin-induced activation of platelets, endothelial cells, brain cells, fibroblasts, smooth muscle cells, or other cells that contain a receptor for thrombin. This function inhibits platelet thrombus formation and other activities mediated by the thrombin receptor.

The BK analogs do not inhibit platelet activation by the same mechanism as intact kininogen and its isolated domain 3. One mM BK analogs do not inhibit $^{125}$I-α-thrombin binding to platelets, as does a molar excess of purified HK, LK, or isolated domain 3. We have found that the BK analogs:

1) block α-thrombin-induced calcium mobilization in platelets;
2) do not inhibit the ability of 1 nM α-thrombin to hydrolyze 0.7 mM of the chromogenic substrate S2238;
3) block 1 nM γ-thrombin from activating platelets in the presence of 100 mg/dl fibrinogen;
4) block α-thrombin from altering expression of the thrombin receptor as detected by monoclonal antibodies SPAN12 and ATAP138;
5) prevent α-thrombin from cleaving the thrombin receptor; and
6) inhibit platelet function in vivo and in vitro.

Without wishing to be bound by any theory, it is believed that BK analogs act to inhibit platelet and other cell activation by inhibiting α-thrombin from cleaving its receptor on platelets and other cells.

According to one embodiment of the invention, the BK analog represents a chain truncation analog of a parent segment from the mature human kininogen heavy chain, which parent segment spans kininogen heavy chain amino acids 333 to 396, wherein the analog includes the core sequence Arg-Pro-Pro-Gly, which core sequence corresponds to kininogen heavy chain residues 363–366.

In a further embodiment, the BK analog represents a chain truncation analog of the kininogen heavy chain parent segment, which peptide contains the core sequence Arg-Pro-Pro-Gly, and up to 7 amino acids from the kininogen heavy chain parent segment upstream (in the amino terminus direction) of the core sequence, and up to 9 amino acids from the kininogen heavy chain parent segment downstream (in the carboxy terminus direction) of the core sequence. More preferably, the amino acids added to the amino terminus and the carboxy terminus of the core sequence are selected from kininogen heavy chain residues 357–363 and 367–383, respectively. The amino acid sequence of the human kininogen heavy chain parent segment is given herein as SEQ ID NO:22. The complete sequence for human kininogen heavy chain can be found in Kellerman et al., Eur. J. Biochem. 154:471–478 (1986), the entire disclosure of which is incorporated herein by reference.

In one embodiment of the invention, naturally occurring or synthetic amino acids having the general formula

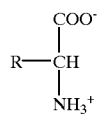

where R is a hydrogen atom or any organic group, have been added to either the carboxyl or amino terminus of a peptide comprising the core sequence (Arg-Pro-Pro-Gly) (SEQ ID NO 20) of the native BK sequence segment (SEQ ID NO: 1) in order to form chain expansion analogs. Preferably, amino acids have been added to either the carboxyl or amino terminus of the five amino acid sequence, Arg-Pro-Pro-Gly-Phe (SEQ ID NO:19). Up to thirty amino acids may be added to either the carboxyl or amino terminus of the core sequence (SEQ ID NO:20) or BK analog SEQ ID NO:19. Preferably, from zero to seven amino acids are added to the amino terminus, and zero to nine amino acids are added to the carboxy terminus of the core sequence (SEQ ID NO:20). More preferably, the peptide comprises the amino acid sequence Arg-Pro-Pro-Gly-Phe (SEQ ID NO:19). An example of the BK analogs included in this invention is the BK analog SEQ ID NO:14 in which two amino acids have been added to the amino terminus and ten amino acids have been added to the carboxyl terminus of the core sequence, Arg-Pro-Pro-Gly (SEQ ID NO:20).

In a further embodiment of the invention, the peptide is HOE 140, having an amino acid sequence of (D-Arg)-Arg-Pro-Hyp-Gly-Thi-Ser-(D-Tic)-Oic-Arg. HOE140 may be purchased from Hoechst, Frankford, Germany or prepared according to the method of Hock et al., Br. J. Pharmacol. 102:758–773 (1991) and Lambeck et al., Br. J. Pharmacol. 102:297–304 (1991), the entire disclosure of which is incorporated herein by reference.

According to another embodiment of the invention, two or more single-chain BK analogs are joined by one or more linkers, L, to form homodimers and heterodimers. As defined herein, homodimers and heterodimers include dimers, trimers, and other multimers. A homodimer is comprised of two or more identical single-chain BK analogs; heterodimers are comprised of two or more different single-chain BK analogs. The linker can be either a covalent bond or a chemical group. In the invention, the number of single-chain BK analogs that can be joined is from two to thiry-two. Preferably, the number of BK analogs joined is from two to twenty, more preferably from two to eight, and most preferably, from two to four. The BK analogs to be joined can be identical or they can be different.

An example of a covalent bond linking two single-chain BK analogs is the disulfide bond formed by the oxidation of two single chain BK analogs containing cysteine amino acids. This may require initially modifying the parent peptide so that the peptide includes a Cys residue in the appropriate position. Cysteine residues on single-chain BK analogs can be oxidized to form BK analog dimers by dissolving 1 mg of the single-chain peptide in 1.5 ml of 0.1% (v/v) 17.5 mM acetic acid, pH 8.4, followed by flushing with nitrogen and then 0.01 M $K_2Fe(CN)_6$. After incubation for one hour at room temperature, the dimer peptide is purified by HPLC.

Another example of a suitable covalent bond for linking two single-chain BK analogs is the amide bond formed by reacting the amino group of a lysine amino acid residue on one chain with the carboxylic acid group of a glutamic or aspartic amino acid residue of another chain.

Alternatively, the linking group can be formed by the covalent bond between two single-chain BK analogs using a cross-linking reagent. For example, homodimers and heterodimers can be prepared by first preparing S-(-N-hexylsuccinimido)-modified peptide monomers according to the method of Cheronis et al., J Med. Chem. 37: 348 (1994). N-hexylmaleimide, a precursor for the modified peptide monomers, is prepared from N-(methoxycarbonyl) maleimide and N-hexylamine by mixing the two compounds in saturated $NaHCO_3$ at 0° C. according to the procedure of Bodanszky and Bodanszky, *The Practice of Peptide Synthesis;* Springer-Verlag, New York, pp. 29–31 (1984). The product of the resulting reaction mixture is isolated by extraction into ethyl acetate, followed by washing with water, dried over $Na_2SO_4$, and is then concentrated in vacuo to produce N-hexylmaleimide as a light yellow oil. S-(N-Hexylsuccinimido)-modified peptide monomers are then prepared from a cysteine-containing peptide (monomer) and N-hexylmaleimide by mixing one part peptide with 1.5 parts N-hexylmaleimide in dimethylformamide (3.3 ml/mM peptide) followed by addition to 30 volumes of 0.1 M ammonium bicarbonate, pH 7.5. The S-alkylation reaction carried out in this manner is complete in 30 min. The resulting S-(N-hexylsuccinimido)-modified peptide monomer is purified by preparative reverse-phase HPLC, followed by lyophilization as a fluffy, white powder.

Bissuccinimidohexane peptide dimers, either as homodimers or heterodimers, may be prepared according to the method of Cheronis et al., supra from cysteine-substituted peptides in the same or different positions, respectively. A mixture of one part bismaleimidohexane is made with two parts peptide monomer in dimethylformamide (3.3 ml/mM peptide) followed by addition to 0.1 ammonium bicarbonate, pH 7.5. The reaction mixture is stirred at room temperature and is usually completed within 30 min. The resulting bissuccinimidohexane peptide dimer is purified by preparative reverse-phase HPLC. After lyophilization the material is a fluffy, white powder.

Covalently cross-linked BK analog dimers of the present invention may be prepared by utilizing homobifunctional cross-linking reagents, e.g., disuccinimidyl tartrate, disuccinimidyl suberate, ethylene glycolbis(succinimidyl succinate), 1,5-difluoro-2,4-dinitrobenzene ("DFNB"), 4,4'-diisothiocyano-2,2'-disulfonic acid stilbene ("DIDS"), and bismaleimidohexane ("BMH"). The cross-linking reaction occurs randomly between the single-chain BK analogs.

Alternatively, heterobifunctional cross-linking reagents may be employed. Such agents include, for example, N-succinimidyl-3-(2-pyridyldithio)propionate ("SPDP"), sulfosuccinimidyl-2-(p-azidosalicylamido)ethyl-1-3'-dithiopropionate ("SASD", Pierce Chemical Company, Rockford, Ill.), N-maleimidobenzoyl-N-hydroxy-succinimidyl ester ("MBS"), m-maleimidobenzoylsulfosuccinimide ester ("sulfo-MBS"), N-succinimidyl(4-iodoacetyl)aminobenzoate ("SIAB"), succinimidyl 4-(N-maleimidomethyl)-cyclohexane-1-carboxylate ("SMCC"), succinimidyl-4-(pmaleimidophenyl)butyrate ("SMPB"), sulfosuccinimidyl (4-iodoacetyl)aminobenzoate ("sulfo-SIAB"), sulfosuccinimidyl 4-(N-maleimidomethyl)cyclohexane-1-carboxylate ("sulfo-SMCC"), sulfosuccinimidyl 4-(p-maleimidophenyl)-butyrate ("sulfo-SMPB"), bromoacetyl-p-aminobenzoyl-N-hydroxy-succinimidyl ester, iodoacetyl-N-hydroxysuccinimidyl ester, and the like.

For heterobifunctional cross-linking, a first single-chain BK analog is derivatized with, e.g., the N-hydroxysuccinimidyl portion of the bifunctional reagent, and the derivatized BK analog is purified by gel filtration. Next, a second single-chain BK analog (which may or may not be the same or different from the first BK analog) is reacted with the second functional group of the bifunctional reagent, assuring a directed sequence of binding between components of the BK dimer.

Typical heterobifunctional cross-linking agents for forming protein-protein conjugates have an amino-reactive N-hydroxysuccinimide ester (NHS-ester) as one functional group and a sulfhydryl reactive group as the other functional group. First, epsilon-amino groups of surface lysine residues of the first single chain BK analog are acylated with the NHS-ester group of the cross-linking agent. The second single chain BK analog, possessing free sulfhydryl groups, is reacted with the sulfhydryl reactive group of the cross-linking agent to form a covalently cross-linked dimer. Common thiol reactive groups include maleimides, pyridyl disulfides, and active halogens. For example, MBS contains a NHS-ester as the amino reactive group, and a maleimide moiety as the sulfhydryl reactive group.

Photoactive heterobifunctional cross-linking reagents, e.g., photoreactive phenyl azides, may also be employed. One such reagent, SASD, may be linked to a single-chain BK analog via its NHS-ester group. The conjugation reaction is carried out at pH 7 at room temperature for about 10 minutes. Molar ratios between about 1 and about 20 of the cross-linking agent to the BK analog may be used.

The purified, derivatized BK analog is collected by affinity chromatography using a matrix having affinity for BK analogs, e.g., a polyclonal antibody reared to the BK analog. Antibody for this purpose may be prepared by coupling the BK analog to key hole limpet hemocyanin using 1-ethyl-3-(3-dimethylaminopropyl)-carbodiimide-HCL (Goodfriend et al., *Science* 144, 1344 (1964)). The resulting conjugate is used to immunize rabbits by the procedure of Müller-Esterl et al., *Methods Enzymol* 163, 240 (1988) to produce anti-BK analog antibodies. The purified antibody is coupled to AFFI-GEL 10 (Bio-Rad, Richmond, Calif.) to form an affinity column. Immobilized anti-BK analog antibody, with the derivatized BK analog bound thereto, is then removed from the column by 0.2 M glycine elution and suspended in a solution of a second single chain BK analog. An ultraviolet light source (e.g., Mineralight UVSL-25, Ultra Violet Products, Inc., San Gabriel, Calif.) is positioned 1 cm from the gently stirred suspension and irradiated in a long-wavelength range for about 10 minutes. The suspension is put back on the anti-BK analog antibody affinity column and washed with a buffer containing 0.15 M NaCl, 0.1% bovine serum albumin, 0.01% polysorbate 80 and 25 KIU/ml of aprotinin to remove reaction byproducts. The covalently cross-linked dimer is eluted with the same buffer system containing 0.2 M glycine or 5 M guanidine. The eluted dimer is dialyzed against buffer to remove the chaotropic agent.

Following reaction with the BK analog under ultraviolet irradiation, and chromatography of the reaction mixture as above, the covalently cross-linked dimer is eluted with either 0.2 M glycine or 5 M guanidine.

While the above-described procedure utilizes SASD, a cleavable cross-linker, non-cleavable cross-linking reagents may be utilized which contain, e.g., alpha-hexanoate, rather than beta-ethyl-1,3-dithiopropopionate moieties. MSB is one example of a non-cleavable cross-linking reagent.

The single-chain BK analogs may be prepared by conventional solid phase peptide synthesis techniques using automated synthesis. Alternatively, BK analogs may be prepared by recombinant DNA techniques. Based upon the known amino acid sequence of bradykinin, a synthetic gene may be constructed corresponding to that sequence, and introduced into an appropriate host by appropriate cloning vectors. Thus, it should be understood that the present invention is not merely limited to the use of BK analogs as prepared by peptide synthetic methods, but also includes the corresponding polypeptide prepared by recombinant techniques.

Moreover, by utilization of such recombinant techniques, one skilled in the art may prepare analogs of native bradykinin such as by site-directed mutagenesis of the relevant DNA, wherein the native amino acid sequence is modified by resultant single or multiple amino acid additions or deletions. All such modifications resulting in a BK analog are included within the scope of the invention provided the molecule substantially retains the ability to inhibit thrombin-induced cell activation.

The BK analogs of the present invention inhibit α-thrombin-induced and ADP-induced platelet aggregation; block α-thrombin-induced calcium mobilization; do not block $^{125}$I-α-thrombin binding to platelets; and prevent α-thrombin from cleaving the thrombin receptor. Protocols for the determination of these activities are set forth in Sections IIA–IIE and Section III, herein respectively.

Purified BK analogs may be administered in any circumstance where inhibition of thrombin-induced or ADP-induced platelet activation or platelet aggregation is sought. They are administered to subjects experiencing platelet thrombosis from any cause or they may be used prophylactically for persons undergoing surgery for insertion of artificial dacron grafts to prevent reocclusion events due to platelet thrombi. They may also be infused into individuals to prevent strokes and cerebral edema.

The peptides may be administered by any convenient means which will result in delivery into the bloodstream in a substantial amount. Intravenous administration is presently contemplated as the preferred administration route, although intranasal administration may also be utilized. Since BK analogs are soluble in water, they may therefore be effectively administered in solution. The actual dosage administered may take into account the size and weight of the patient, whether the nature of the treatment is prophylactic or therapeutic in nature, the age, health and sex of the patient, the route of administration, and other factors. An effective daily dosage of active ingredients based upon in vivo clearance studies involving HK, LK, $D_3$ and SEQ ID NO:19 is from about 3 g per day per 70 Kg of body weight. The preferred dosage is about 3 g per day per 70 kg of body weight given in a single bolus infusion of 2.4 gm followed by a continuous infusion of 0.025 gm/hour. Those skilled in the art should be able to derive appropriate dosages and schedules of administration to suit the specific circumstances and needs of the patient.

The amount of BK analog administered will depend upon the degree of platelet aggregation inhibition desired. While infusion of a sufficient BK analog to achieve 3 g/day dosage may be advantageously utilized, more or less of the peptide may be administered as needed. The therapeutic end point may be determined by monitoring platelet function by aggregation and secretion, bleeding, and vessel patency. The actual amount of the BK analog administered and the length of the therapy regime to achieve the desired intravascular concentration is readily determinable by those skilled in the art by routine methods.

The BK analogs may be administered in a pharmaceutical composition in a mixture with a pharmaceutically acceptable carrier. The pharmaceutical composition may be compounded according to conventional pharmaceutical formulation techniques. The carrier may take a wide variety of forms depending on the form of preparation desired for administration. For a composition to be administered parenterally, the carrier will usually comprise sterile water, although other ingredients to aid solubility or for preservation purposes may be included. Injectable suspension may also be prepared, in which case appropriate liquid carriers, suspending agents and the like may be employed. The preferred parenteral route of administration is intravenous administration.

For intravenous administration, the BK analogs may be dissolved in any appropriate intravenous delivery vehicle containing physiologically compatible substances, such as sterile sodium chloride having a buffered pH compatible with physiologic conditions. Such intravenous delivery vehicles are known to those skilled in the art.

The following experimental section illustrates the practice of the invention.

I. Preparation of High Molecular
Weight Kininoen and BK Analogs

A. Preparation of High Molecular Weight Kininogen

HK was purified from plasma by a modification of the procedures of Johnson et al., *Thromb. Res.* 48, 187 (1987) and Müller-Esterl et al., *Methods Enzymol* 163, 240 (1987). One hundred ml of 1 mM DFP-treated fresh frozen plasma was thawed at 37° C., to which 10 mM benzamidine-HCl, 40 μg/ml Polybrene, 2 mM EDTA, 0.2 mM PMSF, 0.2 mg/ml soybean trypsin inhibitor, 100 U/ml aprotinin and 2 M NaCl were added according to the method of Schmaier et al., *Methods in Enzymology* 169, 276 (1989). The treated plasma was then applied to a 2.5×20 cm column of CM-papain-SEPHAROSE 4B equilibrated in 50 mM phosphate buffer containing 2 M NaCl, 1 mM benzamidine-HCl, 40 μg/mL Polybrene, 0.2 mM PMSF, 0.02% (w/v) $NaN_3$, pH 7.5. The CM-papain-SEPHAROSE 4B column was prepared by the procedure of Johnson et al., *Thromb Res.* 48, 187 (1987). HK and LK were eluted in a single peak after the addition of a 50 mM phosphate buffer solution containing 2 mM EDTA and 0.02% (w/v) $NaN_3$, pH 11.5. Five ml fractions were collected into tubes containing 0.25 ml of a solution consisting of 4 mM PMSF in 1 M sodium acetate, pH 4.2 to bring the final pH to 6.0. The fractions containing HK and LK were then applied to a reactive Blue-Sepharose column (Sigma Chemical Corp, St. Louis, Mo.) equilibrated with 0.01 M sodium acetate pH 6.8 by the methods reported by Hasan et al., *J. Biol. Chem.* 269, 31822 (1994). Bound LK and HK were eluted using the same buffer containing 0.3 M and 2 M NaCl, respectively. HK (120 kDa) and LK (66 kDa) migrated as single bands on reduced SDS-PAGE. HK reacted with monoclonal antibodies to its heavy and light chains by ELISA and western blotting, while LK was recognized only by antibodies directed at its heavy chain. Purified HK retained its procoagulant activity and had a specific activity of 11–22 U/mg as previous reported by Schmaier et al., supra.

B. Preparation of BK Analogs

A number of BK analogs that encompass all or a portion of the native BK sequence (SEQ ID NO:1), including SEQ ID NO:7, SEQ ID NO:8, SEQ ID NO:12, SEQ ID NO:13, SEQ ID NO:14, SEQ ID NO:16, SEQ ID NO:17, and SEQ ID NO:20 and peptides SEQ ID NO:4, SEQ ID NO:5, SEQ ID NO:9, SEQ ID NO:10, SEQ ID NO:11, and SEQ ID NO:15 were synthesized. Each peptide was synthesized on an Applied Biosystems model 431 peptide synthesizer, with the carboxy-terminal amino acid covalently attached to a solid phase support, and succeeding amino acids coupled sequentially to the amino terminus. The carboxyl group on the amino acid to be attached was activated with 2-(1-H-benzotriazole-1-YL)-1,1,3,3-tetramethyluroniumhexofluorophosphate (HBTU) and 1-hydroxybenzotriazole (HOBt). The fluorenyl-methyloxycarbonyl moiety was then attached at the amino-terminal end as a blocking group. All peptides were purified by preparative reverse-phase HPLC. Each of these peptides was colorless, odorless, and, with the exception of SEQ ID NO:15, water soluble. Each peptide was characterized to be homogenous by reverse phase HPLC, mass spectroscopy, and amino acid sequencing. SEQ ID NO: 15 was hydrophobic requiring 0.01% DMSO in order to solubilize it.

C. Preparation of Heterodimer and Four Branch MAP BK Analogs

Single-chain and multi-chain peptides of the BK analogs described herein were prepared according to the following protocols.

1. Preparation of Heterodimer

The individual BK analogs used to prepare the heterodimer were synthesized as described in Section I.B. above. A heterodimer of BK analog SEQ ID NO:19 was prepared by synthesizing SEQ ID NO:19 according to the procedure described in Section I.B. above. At the amino terminus of SEQ ID NO:19, a Nα-(t-butyloxycarbonyl-Nε-9-fluorenyhnethyloxycarbonyl-L-lysine was attached using HBTU and HOBt. Attachment of L-lysine was followed by attachment of N-fluorenyl-methyloxycarbonyl-L-glutamic acid-α-butyloxycarbonyl ester by the same procedure. The glutamic acid's free carboxyl group was then attached to the amine side chain of the L-lysine resulting in a heterodimer rather than a linear amino acid. BK analog SEQ ID NO:19 was then built onto the free amine of the N-fluorenyl-methyloxycarbonyl of the L-glutamic acid. The heterodimer having the formula:

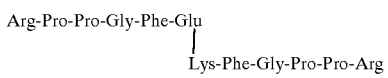

was purified by reverse phase HPLC and the single species was characterized by mass spectroscopy.

2. Preparation of Four Branch MAP

A four-branch MAP of BK analog SEQ ID NO:20, hereinafter called "4-MAP," was prepared. "MAP" is an acronym for "multiple antigenic peptide". The structure for 4-MAP is as follows:

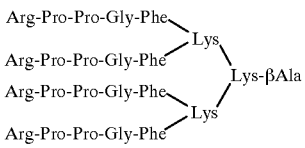

To prepare 4-MAP, a resin core, having a β-alanine attached through its carboxyl group, was joined to a free carboxyl of lysine through the free amine of β-alanine (βAla) to form a lysine-β-alanine complex. Two additional lysine residues were then attached by their free amine groups to the free carboxyl of the first lysine. Four molecules of SEQ ID NO:20 were then attached through their phenylalanine residues to the free amino groups of the two lysine residues, following activation with HBTU and HOBt as described in Section I.D. above. The 4-MAP was purified by reverse phase HPLC and then characterized by mass spectroscopy.

II. Inhibition of Thrombin-Induced Platelet Activation by BK Analogs

The following studies demonstrate that BK analogs corresponding to a region extending from about residue 357 through residue 383 of the heavy chain of HK are useful as inhibitors of thrombin-induced platelet activation.

A. BK Analog Inhibition of Platelet Aggregation and Secretion

The following study demonstrates that the BK analog SEQ ID NO: 14 at a concentration of 1 mM completely inhibits α-thrombin-induced platelet aggregation and secretion while SEQ ID NO:6, a scrambled peptide having the same amino acid count as SEQ ID NO: 14, at 1 mM, produced only 26% inhibition of aggregation and 8% inhibition of secretion after α-thrombin activation. Likewise, a peptide overlapping in sequence with BK analog SEQ ID NO: 14, SEQ ID NO:17 (1 nM), produced only 22% inhibition of aggregation and 4% inhibition of secretion. A series of platelet aggregation and secretion studies were also performed to define the minimal native BK sequence that retained the ability to inhibit α-thrombin-induced platelet activation.

Fresh whole blood was collected and mixed with 0.013 M sodium citrate and platelet-rich plasma was prepared according to the method of Meloni et al., *J. Biol. Chem.* 266, 6786, 1991. Washed platelets were prepared by gel filtration over Sepharose 2B columns in Hepes-Tyrode's buffer (0.137 M NaCl, 3 mM KCl, 0.4 mM Na $H_2PO_4$, 12 mM $NaHCO_3$, 1 mM $MgCl_2$, 14.7 mM Hepes containing 20 mM glucose and 0.2% bovine serum albumin, pH 7.35). Platelets for aggregation and secretion studies were incubated according to the method of Schmaier et al., *Blood* 56, 1013, 1980 with 5-[$^{14}$C]hydroxytryptamine for 30 min at 37° C. The washed platelets ($2\times10^8$/ml, final concentration radiolabeled with 5-[$^{14}$C]hydroxytryptamine) were added to a cuvette of an aggregometer (Chronolog Corp., Havertown, Pa.), standardized using the protocol of Meloni et al., supra. After the addition of $ZnCl_2$, final concentration 50 μM, purified HK (1 μM) or various concentrations of the peptides (0.1 to 3 mM) or buffer alone was added to the cuvette. Once the baseline stabilized, α-thrombin [0.125 U/ml (1 nM) final concentration] was then added to initiate platelet activation. Stirred platelets were allowed to incubate with o-thrombin and additions for 1 min. In other experiments, platelets were stimulated with TRAP (0.625 to 2.5 μM), ADP (1–5 μM) (Sigma), collagen (1.25 μg/ml) (Horm, Munich, Germany), or U-46619 (1 μM)(Calbiochem Behring, San Diego, Calif.). Additional experiments were performed with washed platelets stimulated with γ-thrombin (1 nM) in the presence of human fibrinogen (100 mg/dl). Both γ-thrombin and human fibrinogen were purchased from Enzyme Research Laboratories, South Bend, Ind. At the conclusion of the incubation, the entire platelet sample was centrifuged at 10,900 xg (Model E, Beckman Instruments, Palo Alto, Calif.) over a 0.135 mM formaldehyde, 5 mM EDTA solution (1 part of formaldehyde-EDTA to 4 parts of platelet suspension) and stored on ice until an aliquot of the supernatant was assayed for 5-[$^{14}$C]hydroxytryptamine secretion. Percent secretion was determined by the ratio of the loss of 5-[$^{14}$C]hydroxytryptamine in the supernatant of the agonist-treated specimen to the loss of 5-[$^{14}$C]hydroxytryptamine in the supernatant of the platelet lysate after the value of the control supernatant (i.e., the level of 5-[$^{14}$C] hydroxytryptamine in a unstimulated sample) was subtracted from both.

Figure 1C:
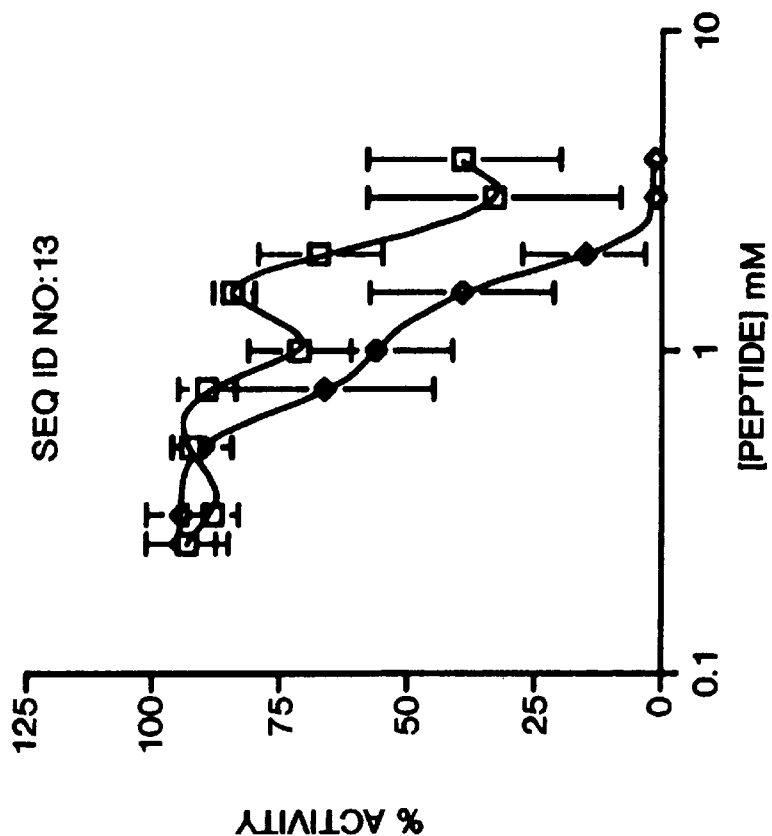

As shown in FIGS. 1A–1C, each peptide that contained the amino acid sequence Arg-Pro-Pro-Gly-Phe (SEQ ID NO:19) produced concentration-dependent inhibition of α-thrombin-induced platelet aggregation and secretion. In all cases, the degree of inhibition of platelet aggregation was greater at a given concentration of peptide than the degree of inhibition of platelet secretion. The most potent thrombin inhibitor among those tested was the BK analog SEQ ID NO:14, which inhibited platelet aggregation and secretion with an $IC_{50}$ of 0.23 and 0.5 mM, respectively (Table I). BK (SEQ ID NO: 1) is also a potent inhibitor of α-thrombin-induced platelet activation with an $IC_{50}$ of 0.25 mM and 1.0 mM for aggregation and secretion inhibition, respectively. The BK analog, SEQ ID NO: 18, which comprises the four carboxy terminal amino acids of the native BK sequence segment, plus twelve additional amino acids, produced only slight inhibition of α-thrombin-induced platelet activation with an $IC_{50} \geq 3$ mM. The BK analog comprising the five amino terminal amino acids of the native BK sequence segment, Arg-Pro-Pro-Gly-Phe (SEQ ID NO:19), inhibited α-thrombin-induced platelet aggregation with an $IC_{50}$ of 0.5 mM. At 1 mM, SEQ ID NO:20 inhibited 95% of platelet aggregation and 25% of secretion, while two scrambled peptides having the amino acid SEQ ID NO:19, SEQ ID NO:5 and SEQ ID NO:9, did not inhibit α-thrombin-induced platelet aggregation and secretion at 1 mM. BK analogs of the mid or carboxy terminal regions of BK, SEQ ID NO:7 and SEQ ID NO:16, were poor inhibitors of α-thrombin-induced platelet activation with $IC_{50} \geq 2$ mM. It would also appear that the amino and carboxyl terminal arginine residues of the native BK amino acid sequence participate in the inhibition of α-thrombin-induced platelet activation. The ability of the BK analogs to block platelet activation was specific for thrombin-induced platelet activation in that the BK analogs did not inhibit collagen-, or U46619-induced platelet aggregation and secretion. Further, BK analogs inhibited γ-thrombin-induced (1 nM) platelet activation in the presence of 100 mg/dl human fibrinogen and in platelet-rich plasma.

TABLE I

INHIBITION OF α-THROMBIN-INDUCED PLATELET
AGGREGATION AND SECRETION BY BK AND BK ANALOGS*

| PEPTIDE | $IC_{50}$ | |
|---|---|---|
| | AGGREGATION | SECRETION |
| SEQ ID NO:14 | 0.23 mM | 0.5 mM |
| BK (SEQ ID NO:1) | 0.25 mM | 1.0 mM |
| SEQ ID NO:12 | 0.5 mM | 1.8 mM |
| SEQ ID NO:8 | 0.85 mM | >2.0 mM |
| SEQ ID NO:13 | 1–1.5 mM | 2–3 mM |
| SEQ ID NO:19 | 0.5 mM | >4.0 mM |
| SEQ ID NO:7 | 2.0 mM | >2.0 mM |
| SEQ ID NO:16 | >3.0 mM | >2.0 mM |
| SEQ ID NO:18 | 3.0 mM | >3.0 mM |

*The data presented are the mean of three or more similar experiments.

B. BK Analog Inhibition of Calcium Mobilization

Further studies were performed to ascertain whether BK analogs inhibit α-thrombin-induced $Ca^{2+}$ mobilization in platelets. Since α-thrombin activation of platelet stimulus response coupling precedes platelet aggregation (Charo et al., *J. Clin. Invest.*, 60, 866 (1977), finding that BK analogs inhibit α-thrombin-induced calcium mobilization indicates that BK analogs interfere with α-thrombin activation of platelets at the level of the stimulus response coupling mechanism.

The cytoplasmic free $Ca^{2+}$ concentration ($[Ca^{2+}]_i$) was measured using the fluorescent $Ca^{2+}$ indicator fura-2 (Molecular Probes, Inc., Eugene, Oreg.). Gel filtered platelets in Hepes-Tyrode's buffer were loaded with fura-2 by incubation at 37° C. with 1 μM fura-2/acetoxymethyl ester for 45 min according to the method of Rasmussen et al., *J. Biol. Chem.* 268, 14322 (1993). The labeled platelets were then re-gel filtered to remove any excess probe. Aliquots of the labeled platelet suspension were transferred into a quartz cuvette with a magnetic stirrer, which was then placed in a thermostatically controlled chamber at 37° C. in a fluorescence spectrophotometer (Dual Wave Length Shimazdu SP5000 Spectrofluorometer, Shimazdu USA, Pittsburgh, Pa.). Reagents were directly added to the cuvette. The excitation wave lengths varied between 340 and 380 nm. The fluorescence was measured by recording emitted light at 510 nm as reported by Fisher et al, *Mol. Pharm.* 35, 195 (1989). The minimum emission was determined on a 20 mM digitonin, 10 mM EGTA solubilized platelet sample; maximum emission was determined on the same sample with 10 mM $Ca^{2+}$ added. The intraplatelet free $Ca^{2+}$ concentration was calculated by the method of Grykiewicz et al., *J. Biol. Chem.* 260, 3440 (1985). The intraplatelet free $Ca^{2+}$ concentration was calculated by the method of Grykiewicz et al., *J. Biol. Chem.* 260, 3440 (1985). The ratio of the fluorescence readings was calculated as R=340/380 nm and processed according to the equation $[Ca^{2+}]_i = K_D((R-R_{min})/(R_{max}-R))(S_{f2}/S_{b2})$ to determine the intraplatelet free $Ca^{2+}$ concentration. The $K_D$ for fura-2 was assumed to be 224 nM. $R_{max}$ and $R_{min}$ are the maximum and minimum fluorescence ratios measured at the end of the experiment, respectively; $S_{f2}$ and $S_{b2}$ are the fluorescence values at 380 nm in the absence and presence of saturating $[Ca^{2+}]$, respectively.

Figure 2D:
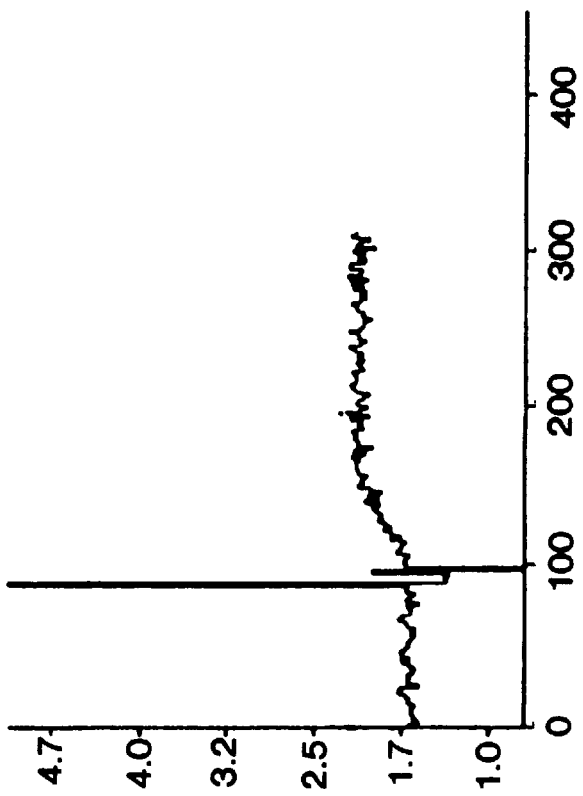
Figure 2C:
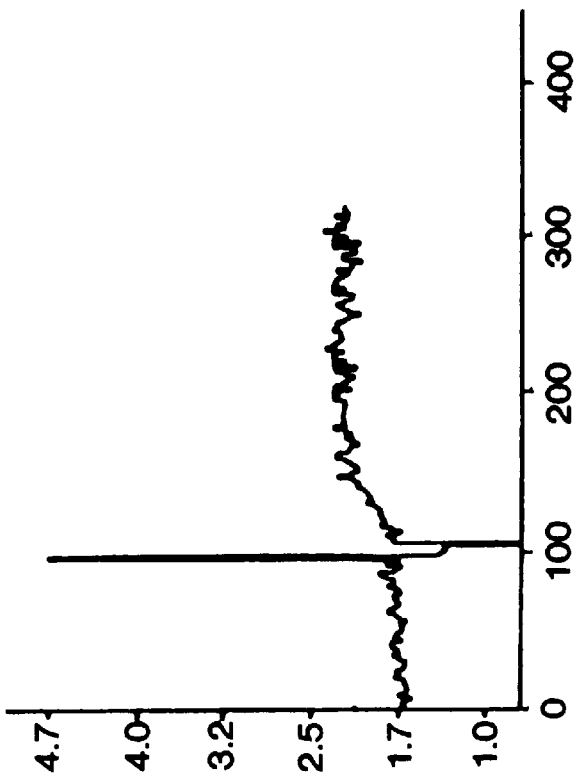
Figure 3:
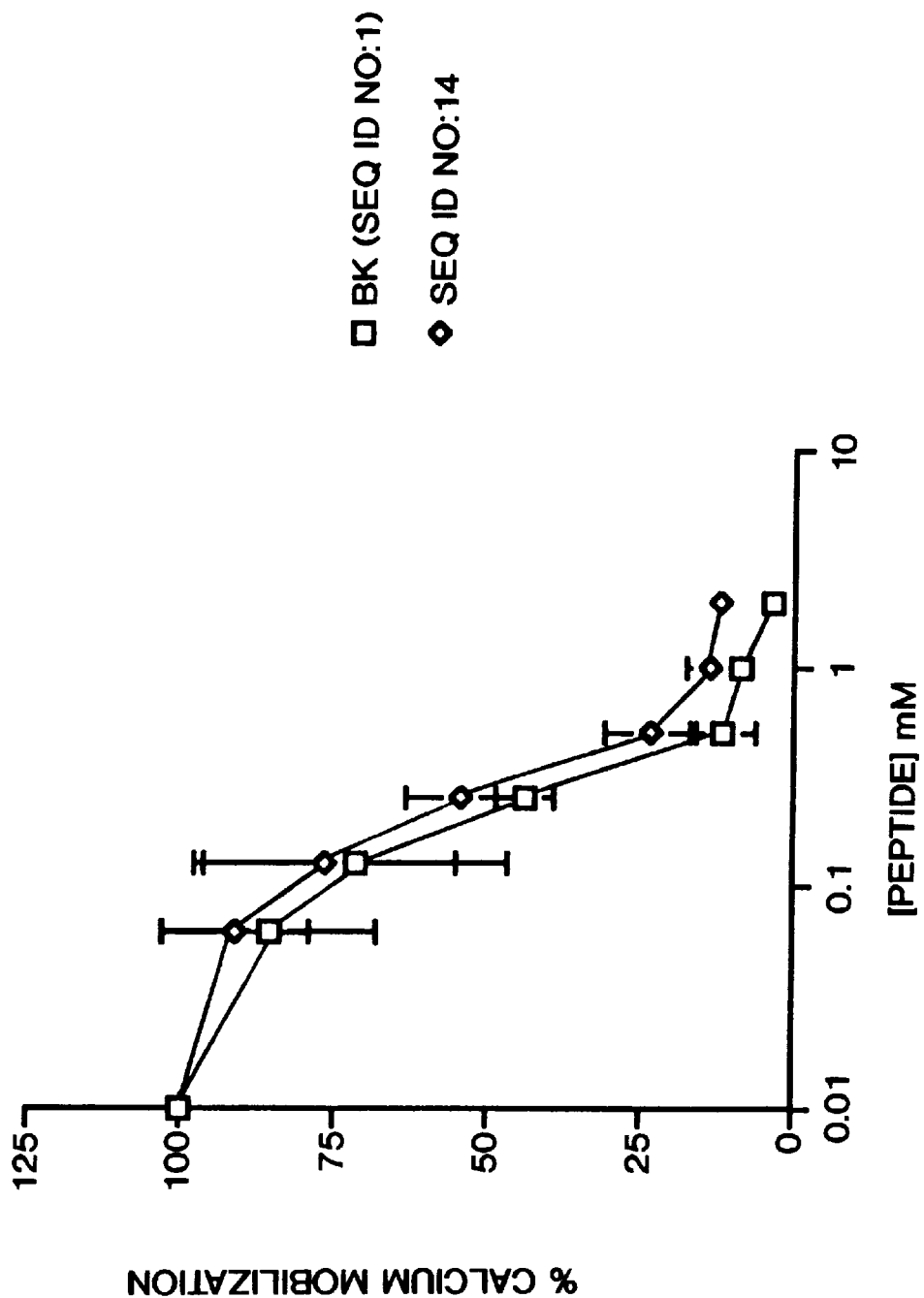
FIG. 3 is a plot of the inhibition of α-thrombin mediated calcium mobilization by BK (SEQ ID NO:1) and BK analog SEQ ID NO:14. Increasing concentrations (0.01 mM to 2 mM) of BK (□) or SEQ ID NO:14 (◇) were incubated with gel filtered platelets before the addition of α-thrombin. The data was plotted as the percent inhibition of $Ca^{2+}$ mobilized in the peptide-treated samples versus an untreated sample. The Figure is the mean ±SEM of the data derived from three identical experiments at each concentration.

As shown in FIG. 2A, thrombin alone induces a substantial change in $Ca^{2+}$ mobilization which was inhibited by HK (FIG. 2B). BK and BK analog SEQ ID NO: 14 block α-thrombin-induced calcium mobilization similar to their parent protein, HK (FIG. 2C and FIG. 2D). Increasing concentrations of BK and BK analog SEQ ID NO:14 produced decreasing $Ca^{2+}$ mobilization with an $IC_{50}$ of 0.23 and 0.3 mM, respectively. The results of the concentration dependent study are presented in FIG. 3.

Figure 4B:
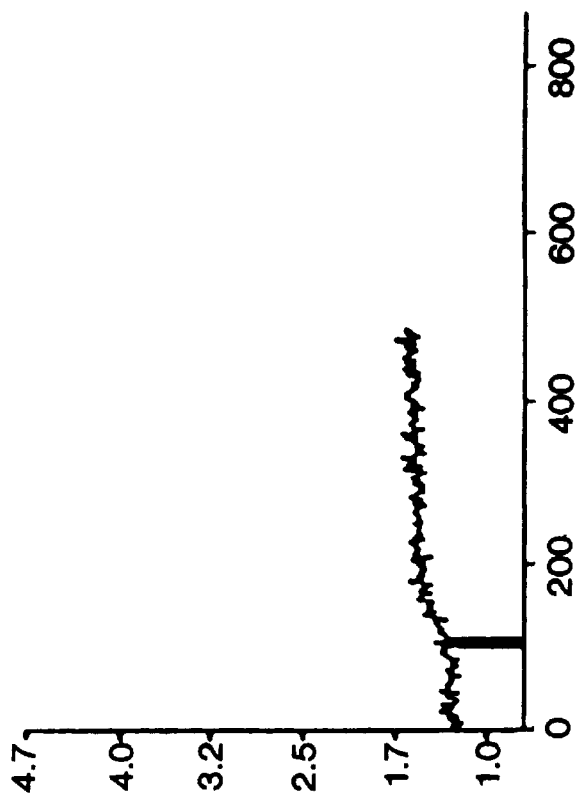
FIGS. 4A–4D are plots of the influence of BK analog SEQ ID NO:19 on α-thrombin-induced calcium mobilization in platelets. Platelets were incubated with 1 nM α-thrombin in the absence of (4A) or presence of SEQ ID NO:19 at a concentration of 1.0 mM (4B), 0.5 mM (4C) and 0.125 (4D). Each figure is a representative experiment of several experiments.
Figure 4A:
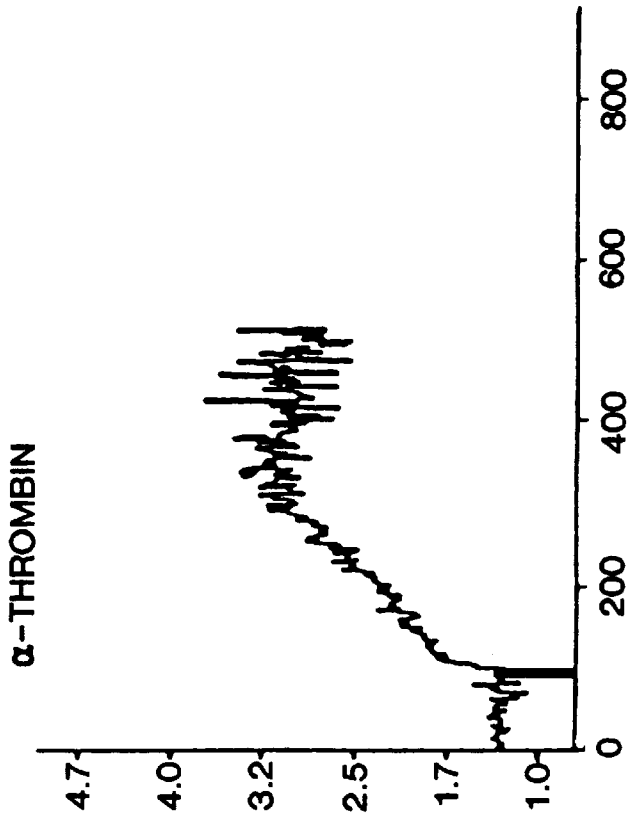
Figure 4D:
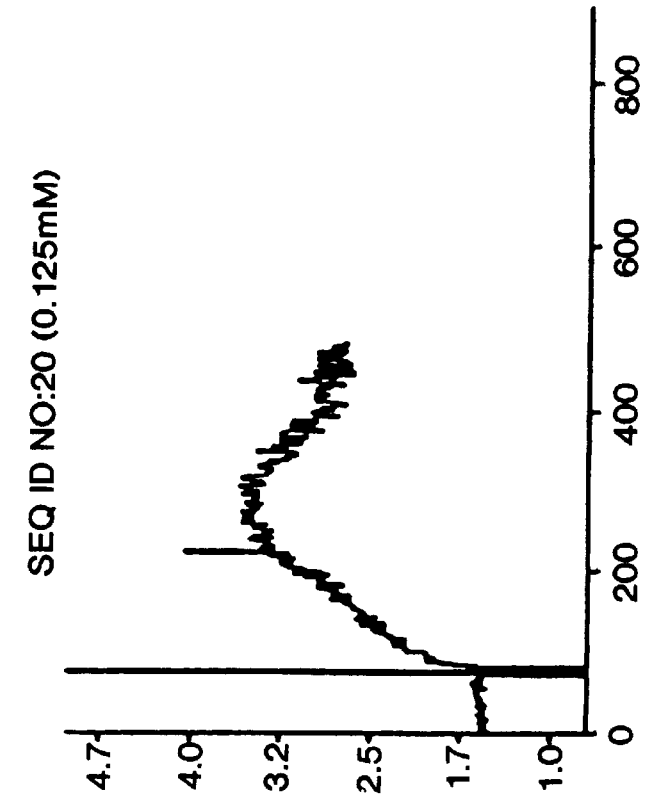
Figure 4C:
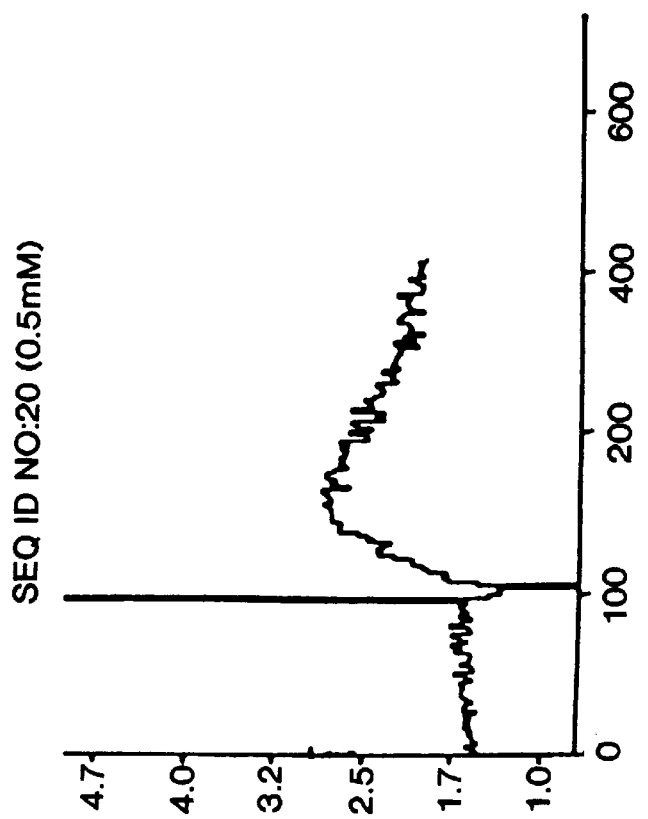

It was also found that SEQ ID NO:19 was able to inhibit α-thrombin-induced calcium mobilization in a concentration dependent manner. One mM of BK analog SEQ ID NO:19 produced 80% inhibition of α-thrombin-induced calcium mobilization (FIG. 4B). When the concentration of the BK analog SEQ ID NO:19 was reduced to 0.5 mM and 0.125 mM, the level of α-thrombin-induced calcium mobilization returned to levels exhibited in the absence of a α-thrombin inhibitor (FIG. 4A). The results are shown in FIGS. 4C and 4D, respectively. These data indicate that BK analogs interfered with α-thrombin activation of platelets at the level of the stimulus-response coupling mechanism.

C. BK Analogs Do Not Inhibit $^{125}$I-α-Thrombin Binding to Platelets

An $^{125}$I-α-thrombin binding study was conducted to determine if the BK analogs described herein inhibited iodinated α-thrombin binding to platelets.

Gel filtered platelets were placed into polypropylene tubes and diluted with Hepes-Tyrode's buffer, containing 2 mM $CaCl_2$ and 50 μM $ZnCl_2$ and additions, to a final concentration of 2×10$^8$ platelets/ml. The reaction was started by the addition of 1 nM $^{125}$I-α-thrombin, which was prepared by using the iodogen technique as reported by Meloni et al., *J. Biol. Chem.* 266, 6786 (1991). Incubations were performed at 37° C. for specified times with various additions. After incubation, 50 μl aliquots were removed in triplicate for each experimental point and placed in polypropylene microcentrifuge tubes with an extended tip containing 200 μl of an oil mixture which consisted of 1 part Apiezon A oil to 9 parts of n-butylphthalate (Gustafson et al., *J. Clin. Invest.* 78, 810 (1986)), and centrifuged at room temperature for 2 min at 10,900× g in a microcentrifuge. (Model E, Beckman Instruments, Palo Alto, Calif.) The supernatant was removed and the tips amputated for placement in the gamma counter. The radioactivity present in the cell pellet was determined with an LKB Rack Gamma Counter (LKB Instruments, Inc., Gaithersburg, Md.). Nonspecific binding was measured in the presence of a 100-fold molar excess of α-thrombin.

Figure 5:
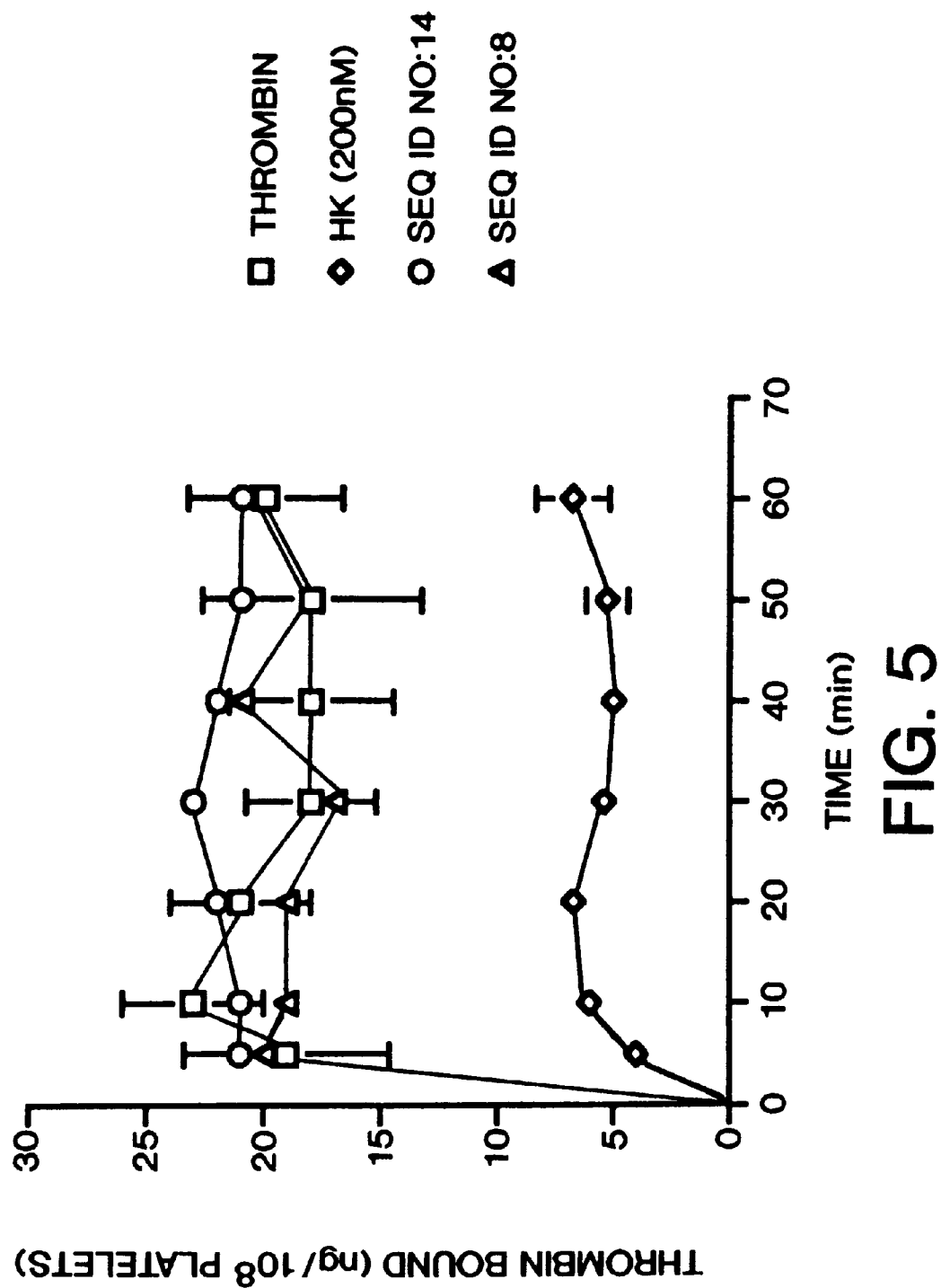
FIG. 5 is a plot of the inhibition of $^{125}$I-α-thrombin binding to platelets in the absence (□) or presence of 200 nM HK (◇), 1 mM of the BK analog SEQ ID NO:14 (○), or 1 mM of the BK analog SEQ ID NO:8 (Δ). The Figure is the mean ±SEM of the data derived from three experiments.

The data plotted in FIG. 5 are the mean of three experiments and indicates that 200 nM HK was able to inhibit proteolytically active α-thrombin from binding to platelets. On the contrary, although BK analogs are good inhibitors of α-thrombin-induced platelet aggregation, secretion, and calcium mobilization at 1 mM concentration, the BK analogs SEQ ID NO: 14 and SEQ ID NO:8 did not block $^{125}$I-α-thrombin binding to washed platelets. These data indicated that the mechanism by which BK analogs inhibit α-thrombin-induced platelet activation is different than that produced by HK, LK, or D3, i.e., they do not block $^{125}$I-α-thrombin binding to platelets.

D. Mechanism of BK Analog Inhibition of α-Thrombin Activation of Platelets as Determined by Flow Cytometry Flow cytometry studies were performed to determine whether BK analogs prevent α-thrombin from eliminating an epitope on the thrombin receptor which is lost following α-thrombin cleavage- of the receptor. SPAN12 is an antibody to the thrombin receptor on platelets, which is specific for such an epitope. Studies were also performed to determine the effect of BK analogs on an epitope recognized by monoclonal antibody ATAP 138. The antibody is directed to an epitope on the thrombin receptor which is preserved after α-thrombin cleaves the receptor (FIGS. 7A–7D).

Monoclonal antibody SPAN12 was reared to the 12 amino acids, Asn-Ala-Thr-Leu-Asp-Pro-Arg-Ser-Phe-Leu-Leu-Arg (SEQ ID NO:2), that bridge the α-thrombin cleavage site on the thrombin receptor by the methods of Molinot et al., *J. Biol. Chem.* 270:ln Press, 1995. Monoclonal antibody ATAP138 recognizes the epitope Asn-Pro-Asn-Asp-Lys-Tyr-Glu-Pro-Phe (SEQ ID NO:3) on the thrombin receptor which is preserved after cleavage by α-thrombin as reported by Brass et al., *J. Biol. Chem.* 267, 13795 (1992). Monoclonal antibodies to the thrombin receptor, SPAN12 and ATAP138, were obtained from Dr. Lawrence F. Brass of the University of Pennsylvania, and were prepared according to the method of Brass et al., supra.

Platelets for flow cytometry studies were prepared from 53.3 ml fresh blood anticoagulated with 8.7 ml acid citrate dextrose (10 mM trisodium citrate, 66 mM citric acid, 111 mM glucose, pH 4.6). Washed platelets from platelet-rich plasma were prepared by centrifugation at 180× g for 15 min. at room temperature. The platelet-rich plasma was brought to a final concentration of 2.8 μM with PGE1 (Sigma) and 1:25 (vol:vol) with 1 M sodium citrate. After a 5 min. incubation at room temperature, the platelet-rich plasma was centrifuged at 1200× g for 10 min. at room temperature. The platelet pellet was then re-suspended in 10 ml of platelet wash buffer (128 mM NaCl, 4.26 mM NaH$_2$PO$_4$, 7.46 mM Na$_2$HPO$_4$, 4.77 mM sodium citrate, 2.35 mM citric acid, 5.5 mM glucose, 3.5 mg/ml bovine serum albumin, pH 6.5) followed by centrifugation at 1200× g for 5 min. at room temperature. After re-suspension in 5 ml of platelet suspension buffer (137 mM NaCl, 2.6 mM KCl, 13.8 mM NaHCO$_3$, 5.5 mM glucose, 1 MM MgCl$_2$, 0.36 mM NaH$_2$PO$_4$, 10 mM Hepes, 3.5 mg/ml bovine serum albumin, pH 7.35), the platelet count was adjusted to 400,000/μl. One hundred μl of washed platelets were then placed in a 5 ml roundbottom polystyrene tube and were subjected to varying treatments, which included exposure to or in the absence of the BK analogs and/or incubation for 5 min. with or without the platelet agonist, α-thrombin (0.125 U/ml or 1 nM). Primary antibodies were added at a final concentration of 2 μg/ml and the antibodies were incubated with the platelets for 30 min at 4° C. After incubation, the platelets were diluted with 500 μl of platelet suspension buffer and again centrifuged at 1200× g for 5 min. at room temperature. The platelet pellets were then re-suspended in 100 μl of platelet suspension buffer and incubated with a 1:40 dilution of an anti-mouse IgG conjugated with FITC. After an additional incubation for 30 min. at 4° C., the platelets were again centrifuged at 1200× g for 5 min. followed by re-suspension in 500 μl of platelet suspension buffer.

Mouse IgG and an antibody to the epitope CD62 were used as controls. Mouse IgG (Code #4350) was purchased from BioSource, Camarillo, Calif. The fluorescence of bound FITC-anti-IgG to platelets was monitored on an Epics-C flow cytometer (Coulter Electronics, Hialeah, Fla.). Light scatter and fluorescence channels were set at logarithmic gain. Laser excitation was at 488 nm. Green fluorescence was observed through a 525 nm band pass filter. The relative fluorescence intensity of at least 15,000 platelets was analyzed in each sample. An antibody to CD62 (P-selectin) was purchased from Becton-Dickinson (Catalogue #550014), San Jose, Calif.

Figure 6F:
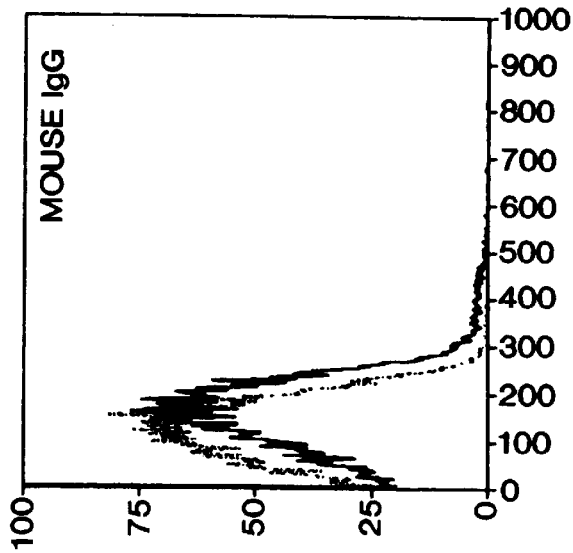
Figure 6E:
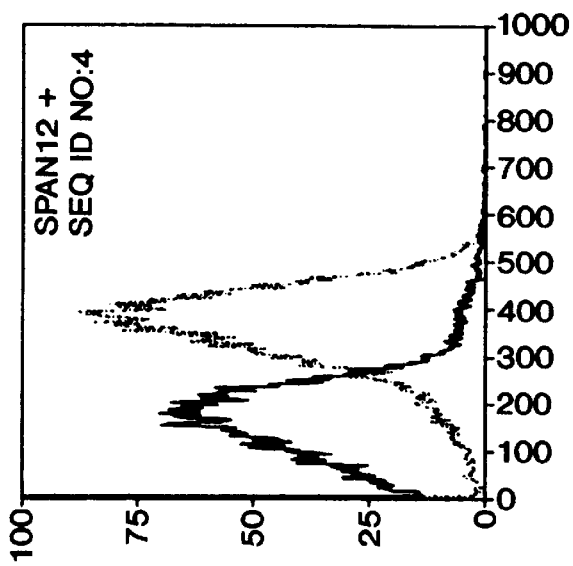
Figure 6D:
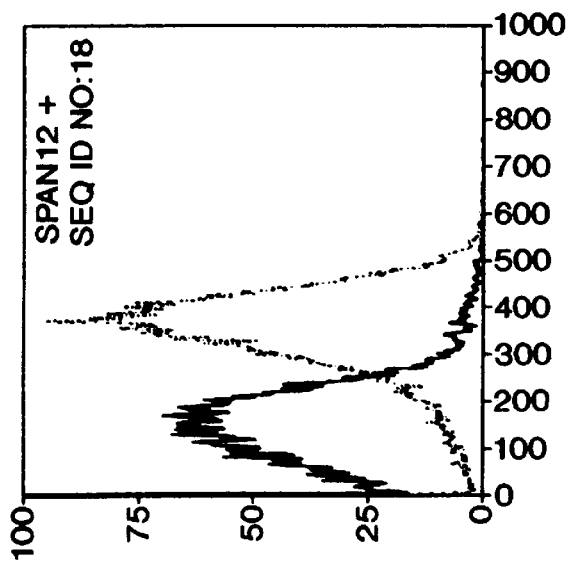

As seen by the forward scatter of the flow cytogram (FIG. 6A, ghost curve), SPAN12 detects an antigen on the thrombin receptor on unstimulated platelets. A thrombin receptor was described by Vu et al., *Cell* 64, 1057 (1991). When the washed platelets were treated with 1 nM α-thrombin (FIG. 6A, solid curve), there was a decrease in the antigenic expression of the epitope of the monoclonal antibody SPAN12. The forward scatter of the SPAN12 epitope seen on unstimulated platelets (ghost curve of FIG. 6A) was shifted towards the origin on α-thrombin activated platelets (solid curve, FIG. 6B) giving an absent antigen detection pattern similar to that for mouse IgG (FIG. 6F) used as a control. The presence of 1 mM BK and the BK analog SEQ ID NO: 14 prevents the loss of the epitope of the thrombin receptor on α-thrombin activated platelets (1 nM) (FIGS. 6B and 6C.) However, 1 nM SEQ ID NO: 17, a BK analog that partially overlaps the amino acid sequence of BK analog SEQ ID NO: 14, or 1 nM of an unrelated peptide (SEQ ID NO:4) having an amino acid content similar to BK analog SEQ ID NO:14, did not prevent α-thrombin from altering the epitope to SPAN12 (FIGS. 6D and 6F). Without wishing to be bound by any theory, these studies suggest that the BK analogs function by actually preventing α-thrombin from cleaving its cloned receptor.

Figure 7B:
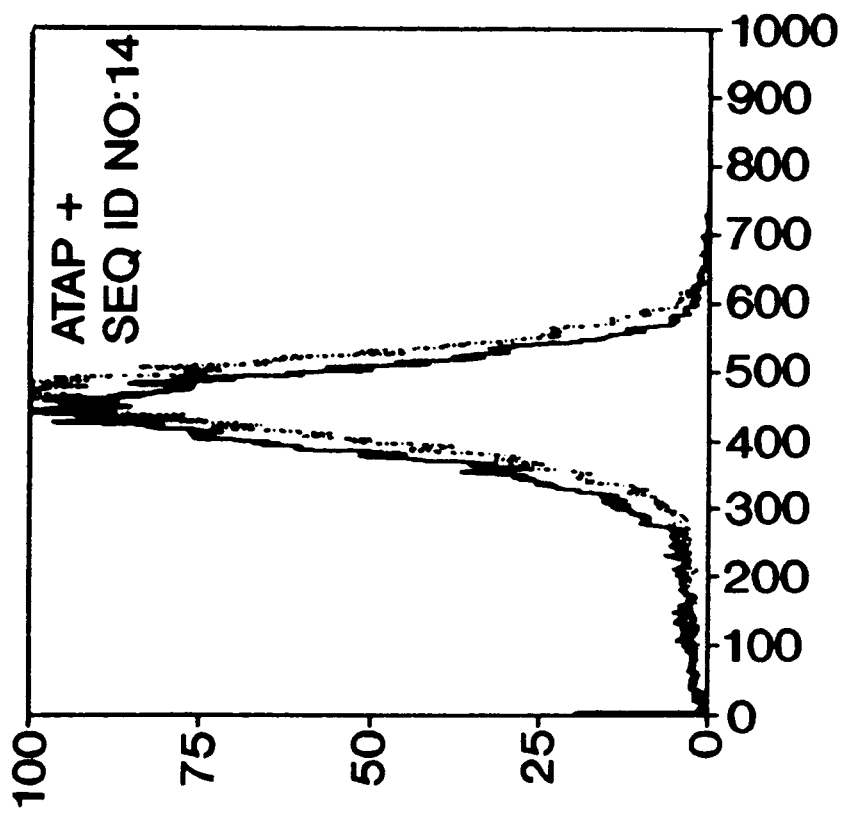
Figure 7A:
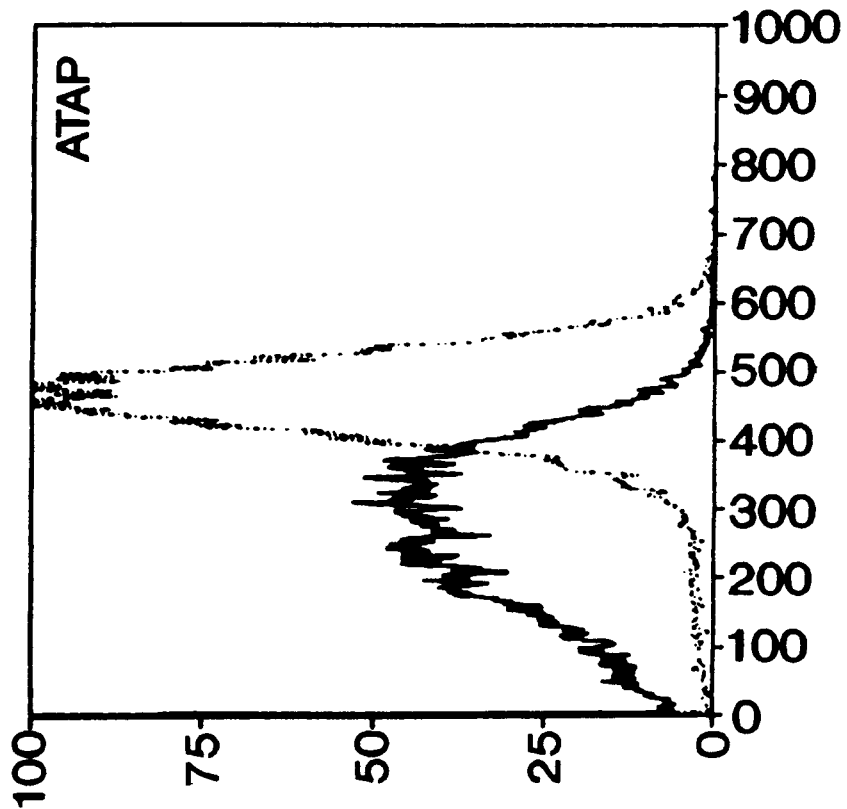

The decrease seen in the extent of the epitope expression of ATAP138 between activated (solid curve) and unactivated platelets (ghost curve) (FIG. 7A) represents internalization of the platelet thrombin receptor after activation as suggested by Hoxie et al., *J. Biol. Chem.* 268, 13756 (1993) and Brass et al., *J. Biol. Chem.* 269, 2943 (1994). The BK analog SEQ ID NO:14 blocked α-thrombin from removing the epitope of the monoclonal antibody ATAP138 (FIG. 7B). Control experiments were also performed with Mouse IgG (FIG. 7C) and an epitope to CD62 (FIG. 7D) which demonstrate no shift in the flow cytogram before and after α-thrombin activation.

E. BK Analogs Prevent α-Thrombin from Cleaving the Thrombin Receptor

A further study was performed to determine whether BK analogs prevent α-thrombin from cleaving the thrombin receptor reported by Vu et al., *Cell* 64, 1057 (1991). A peptide, NAT12 (SEQ ID NO:2), which spans amino acids 55–46 of the α-thrombin cleavage site on the thrombin receptor, was used to determine whether the BK analogs described herein blocked α-thrombin cleavage of the cloned receptor.

The cleavage study was performed according to the method of Molino et al., *J. Biol. Chem.* 270,11168(1995), inwhichNAT12(SEQ ID NO:2) was dissolved in a solution of 0.01 M NaH$_2$PO$_4$ and 0.15 M NaCl, pH 7.4. The mixture was then incubated with 8 nM α-thrombin for one hour at 37° C. either in the absence (control) or presence of 1 mM of BK analog SEQ ID NO:19, or in the presence of 1 mM of a non-BK analog (SEQ ID NO:21), or in the presence of 300 nM HK. Following incubation, each mixture was separated by applying the mixture to a Vyadec C-18 HPLC column in 0.1% trifluoroacetic acid and eluting the mixture with a gradient from 0% to 100% of 80% MeCN and 0.1% trifluoroacetic acid and eluting the mixture with a gradient from 0% to 100% of 80% MeCN and 0.1% trifluoroacetic acid. The size of the separated products were confirmed by mass spectrometry.

Figure 8A:
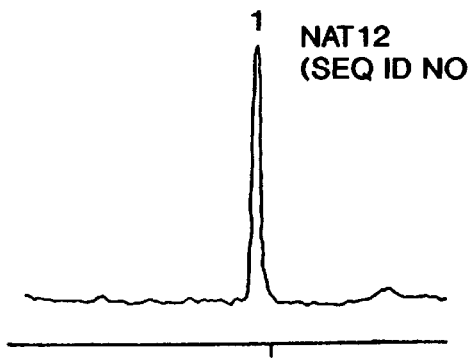
FIGS. 8A–8F are chromatographs showing the influence of BK analog SEQ ID NO:19 and a non-BK analog peptide (SEQ ID NO:21) on α-thrombin-induced cleavage of the thrombin receptor peptide NAT12 (SEQ ID NO:2). NAT12 (SEQ ID NO:2) was incubated in the absence (FIG. 8A) or presence of α-thrombin (FIG. 8C). NAT12 (SEQ ID NO:2) was incubated with α-thrombin in the absence (FIG. 8C) or presence of BK analog SEQ ID NO:19 (FIG. 8D).

As shown in FIG. 8A, NAT12 (SEQ ID NO:2) when measured by HPLC, produced a single peak. Peak 1 of FIG. 8A represents 100%. When NAT12 (SEQ ID NO:2) was treated with (α-thrombin (FIG. 8C, peak 1), its peak area was reduced by 81% and two new peaks appeared to its left, constituting 44% (peak 3) and 37% (peak 2), respectively, of the original peak area (FIG. 8A). The additional peaks, peaks 3 and 2, shown in FIG. 8C, represent the cleavage products of NAT12. In the presence of BK analog SEQ ID NO:19 (FIG. 8D), peak 1 of NAT12 (SEQ ID NO:2) was reduced by 57% after treatment with α-thrombin. The cleavage products of NAT12 (FIG. 8D, peaks 3 and 2) constitute 31% and 26%, respectively, of the non-treated peak area (FIG. 8A).

Figure 8B:
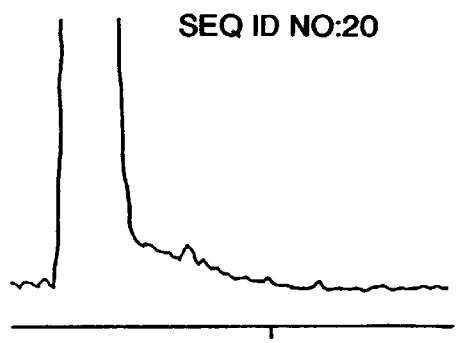
Figure 8C:
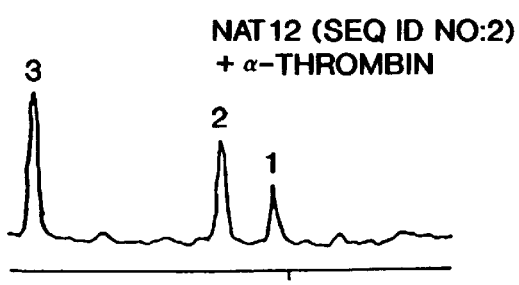
Figure 8D:
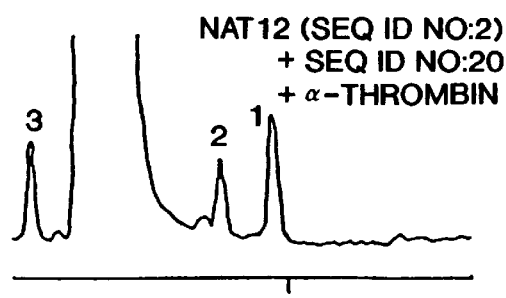
Figure 8E:
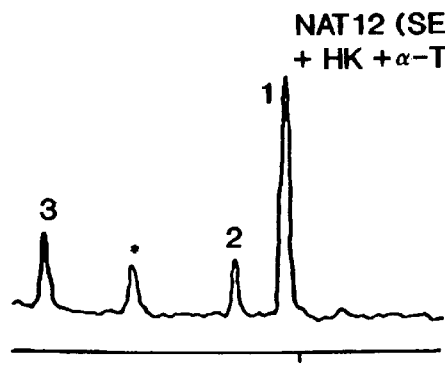

FIG. 8B represents the chromatograph for isolated BK analog SEQ ID NO:20. When NAT12 (SEQ ID NO:2) was treated with α-thrombin in the presence of BK analog SEQ ID NO:19, the peak for BK analog SEQ ID NO:19 appeared between those for the α-thrombin cleavage products (FIG. 8D, peaks 3 and 2). In the presence of 100 nM HK, α-thrombin reduced the size of the original peak for NAT12 (SEQ ID NO:2) (FIG. 8A) by only 32% (FIG. 8E). Moreover, the two α-thrombin cleavage fragments, peaks 3 and 2 in FIG. 8E, constituted only 18% and 14%, respectively, of the area of peak 1 in FIG. 8A. The fourth peak seen in FIG. 8E represented a peak from the HK preparation and is not an additional α-thrombin cleavage fragment.

Figure 8F:
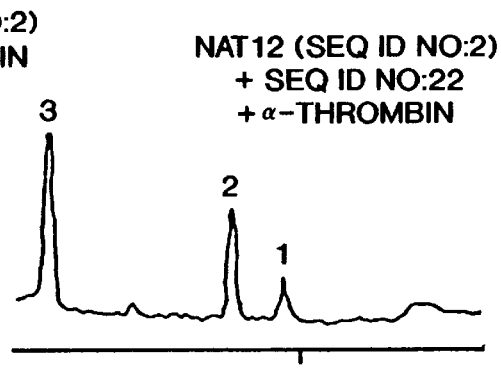

When the non-BK analog (derived from domain 3 of kininogen) (SEQ ID NO:21) was reacted with NAT12 (SEQ ID NO:2), no protection from α-thrombin cleavage was observed (FIG. 8F). In the presence of the non-BK analog (SEQ ID NO:21), α-thrombin produced an 86% reduction in peak area (FIG. 8F) as compared to intact NAT12 (SEQ ID NO:2) (FIG. 8A) with 54% and 32% of the peak area reduced in peaks 3 and 2, respectively (FIG. 8F), relative to peak 1 (FIG. 8A).

These results confirm that the BK analogs described herein prevented α-thrombin from cleaving the cloned thrombin receptor. It is believed that this represents a novel mechanism of inhibition of α-thrombin activation of platelets.

III. BK Analogs Inhibit Platelet Function In Vivo and In Vitro

Additional studies were carried out to demonstrate that the BK analogs described herein inhibit thrombin-induced platelet activation in vivo in rabbits and in vitro in human platelets.

A. Rabbit Clearance and Function Inhibition Study

Clearance studies have been performed in New Zealand white rabbits with BK analog SEQ ID NO:19. White rabbits weighing between 2.0 and 2.5 kg were premedicated according to the method of Michelson et al., *J. Mol. Cell Cardiol.* 20, 547 (1988) with 10 mg/kg 1 M xylazine and 10 mg/kg 1 M ketamine. After tracheostomy, intubation, and positive pressure ventilation done with room air (Harvard instruments), stage III surgical anesthesia was maintained with 20 mg/ml of intravenous pentobarbital. A carotid artery and a jugular vein were then exposed. A catheter was inserted into the exposed carotid artery for withdrawal of blood samples and monitoring the animal's blood pressure (Gould, Inc., Cardiovascular Products, Oxnard, Calif.). In a similar manner, a catheter was inserted into the exposed jugular vein for administering the anesthetic and BK analog SEQ ID NO:19.

For the clearance study, a single bolus of BK analog SEQ ID NO:19 was injected. The amount of BK analog SEQ ID NO:19 injected was calculated from the weight of the animal such that the blood volume was 1 mM with peptide. For example: for a 2.5 kg rabbit, 7% of its weight gives an estimated blood volume of 175 ml. Accordingly, 89 mg of BK analog was injected to make the 175 ml plasma sample 1 mM. Depending upon the size of the animal, 75 to 90 mg peptide was injected. Blood samples were collected at 2, 4, 6, 8, 10, 20, 30, 40, 60, 90, and 120 minute intervals after infusion into a 0.013 M sodium citrate anticoagulant solution. Plasma was prepared from each of the blood samples collected over time by centrifugation of the blood samples at 10,00 xg for two minutes. Aliquots of the plasmas were assayed for the presence of the BK analog SEQ ID NO:19 antigen by the ELISA technique using a MARKIT-M [1–5] BK assay from Dainippon Pharmaceutical Co., Ltd., Osaka, Japan.

For the function inhibition study, other New Zealand white rabbits weighing between 2.0 and 2.5 kg were surgically prepared as described above. After a single bolus infusion of BK analog SEQ ID NO:19 calculated as described above, 5 ml blood samples were collected at 2, 6, 10, 30, 60, 90, 120, 150, 180, 210, and 240 minute intervals following infusion into a 0.013 M sodium citrate anticoagulant solution. The collected blood samples were centrifuged at 180 xg (1000 rpms) for 15 minutes at room temperature. The platelet-rich plasma (PRP) portion of the blood was contained in the supernatant. The platelet count of the PRP, obtained with an H-10 Cell counter (Texas International Laboratories, Inc., Houston, Tex.), was adjusted with rabbit platelet-poor plasma to 200,000–250,000 platelets/μl.

Platelet aggregation studies on the PRP were conducted on a 4-channel aggregometer (BioData-PAP-4, Bio Data Corp., Hatboro, Pa.). The degree of platelet aggregation was determined by measuring the increase in light transmission through a stirred suspension of PRP maintained at 37° C. Platelet aggregation was induced in the PRP sample by addition of 20 μM ADP and γ-thrombin according to the method of Harfenist et al., *Thromb. Haemost.* 53, 183 (1985). Gamma-thrombin (Enzyme Research Laboratories, South Bend, Ind.) was used for this study in lieu of α-thrombin because it does not proteolyze fibrinogen and clot platelet-rich plasma. Like human platelets, rabbit platelets display a variable response to γ-thrombin. Each rabbit's platelets were evaluated before BK analog infusion for their threshold response to γ-thrombin. The rabbit platelets used in this experiment were responsive to 10 nM to 40 nM γ-thrombin. Simultaneous γ-thrombin-induced platelet aggregation studies were performed with 10, 20, and 40 nM γ-thrombin and 20 μM ADP.

Figure 9:
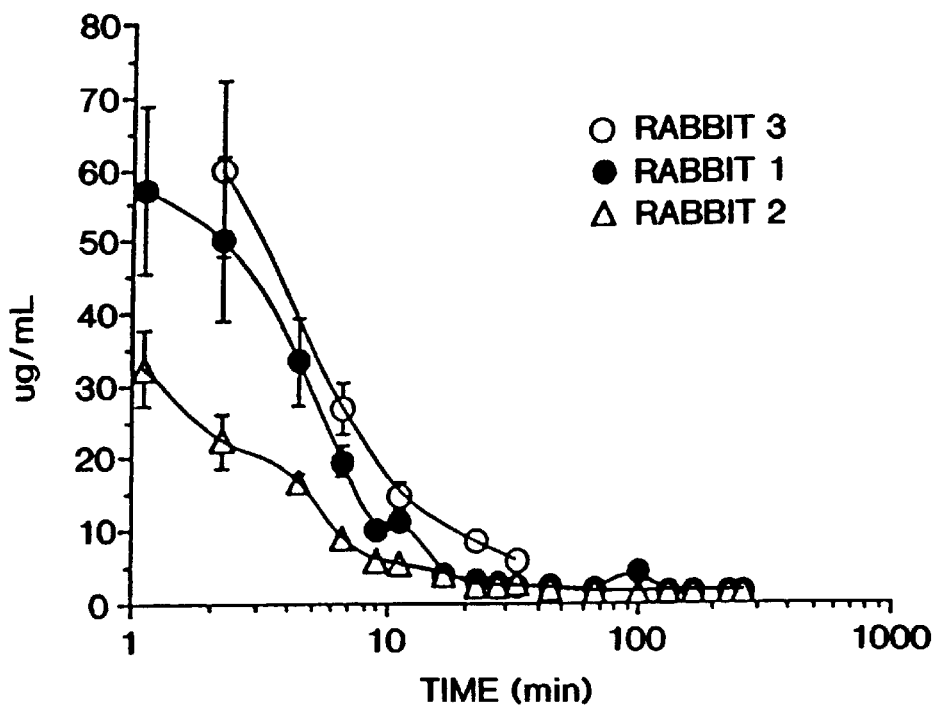
FIG. 9 is a plot of the plasma concentration of BK analog SEQ ID NO:19 in three rabbits following infusion of BK analog SEQ ID NO:20.

As shown in FIG. 9, the peak plasma concentration of BK analog SEQ ID NO:19 after infusion was 60 mg/ml (0.120 mM) for two of three rabbits, as determined by ELISA. No unfavorable effects were observed in the animals following the bolus injection of the BK analog. The rabbits' blood pressure, pulse, and platelet count remained stable and there was no abnormal bleeding at the surgical sites of cutdowns and intubations. The half-life of BK analog SEQ ID NO:19 antigen clearance in plasma was calculated to be 6.6 minutes after infusion. Clearance of BK analog SEQ ID NO:19 initially was not due to renal excretion, as ligating the animal's renal arteries did not lengthen the half-life of the agent (FIG. 9, Rabbit 2). Therefore, the major determinant of the immediate clearance of the BK analog SEQ ID NO:19 antigen was attributed to binding and/or metabolism.

Figure 10:
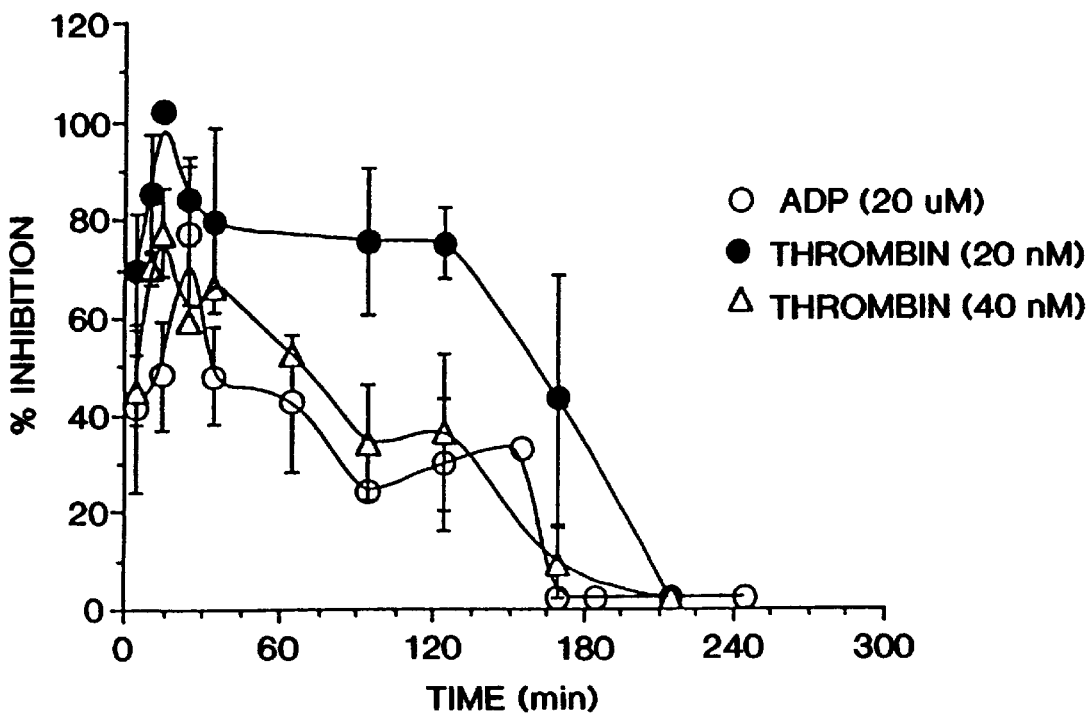
FIG. 10 is a plot of the inhibition of thrombin- or ADP-induced rabbit platelet aggregation over time after a single infusion of BK analog SEQ ID NO:19. (○), 20 μM ADP; (●), 20 nM γ-thrombin; (Δ) 40 nM γ-thrombin.

However, as shown in FIG. 10, BK analog SEQ ID NO:19 had a prolonged biologic clearance. After a single bolus infusion of BK analog SEQ ID NO:19, 10 nM γ-thrombin-induced platelet aggregation was inhibited 100% for over 4 hours (data not shown), 20 nM γ-thrombin-induced platelet aggregation was inhibited ≧50% for 2.75 hours, and 40 nM γ-thrombin-induced platelet aggregation was inhibited ≧50% for one hour. The data further indicated that there was ≧50% inhibition of ADP-induced platelet aggregation for roughly 45 minutes. This latter finding suggested that thrombin mediates ADP-induced platelet activation in vivo as well. Taken together, the data demonstrates that after a single bolus infusion of BK analog SEQ ID NO:19, having a peak peptide concentration of only 0.120 mM two minutes after infusion, the BK analogs described herein were able to have a prolonged, selective inhibitory effect on thrombin-induced platelet activation in vivo.

B. BK Analogs Inhibit Thrombin-Induced Platelet Activation In Human Platelets In Vitro Similar to the in vitro platelet aggregation study done with the New Zealand white rabbits, a study was performed using human platelets to determine if BK analogs inhibit thrombin-induced platelet activation in vitro.

The protocol for the human platelet study was identical to that for the functional study with white rabbits described above in Section III.A, with the following differences.

Blood samples were obtained from normal human volunteers. Platelet counts were measured with a Coulter counter, Model 2F (Coulter, Hialeah, Fla.,) and adjusted to a platelet count of 200,000 platelets/μl. Each individual's platelets at baseline were measured for their threshold response to γ-thrombin. Typical threshold levels were between 10 nM to 40 nM.

Figure 11:
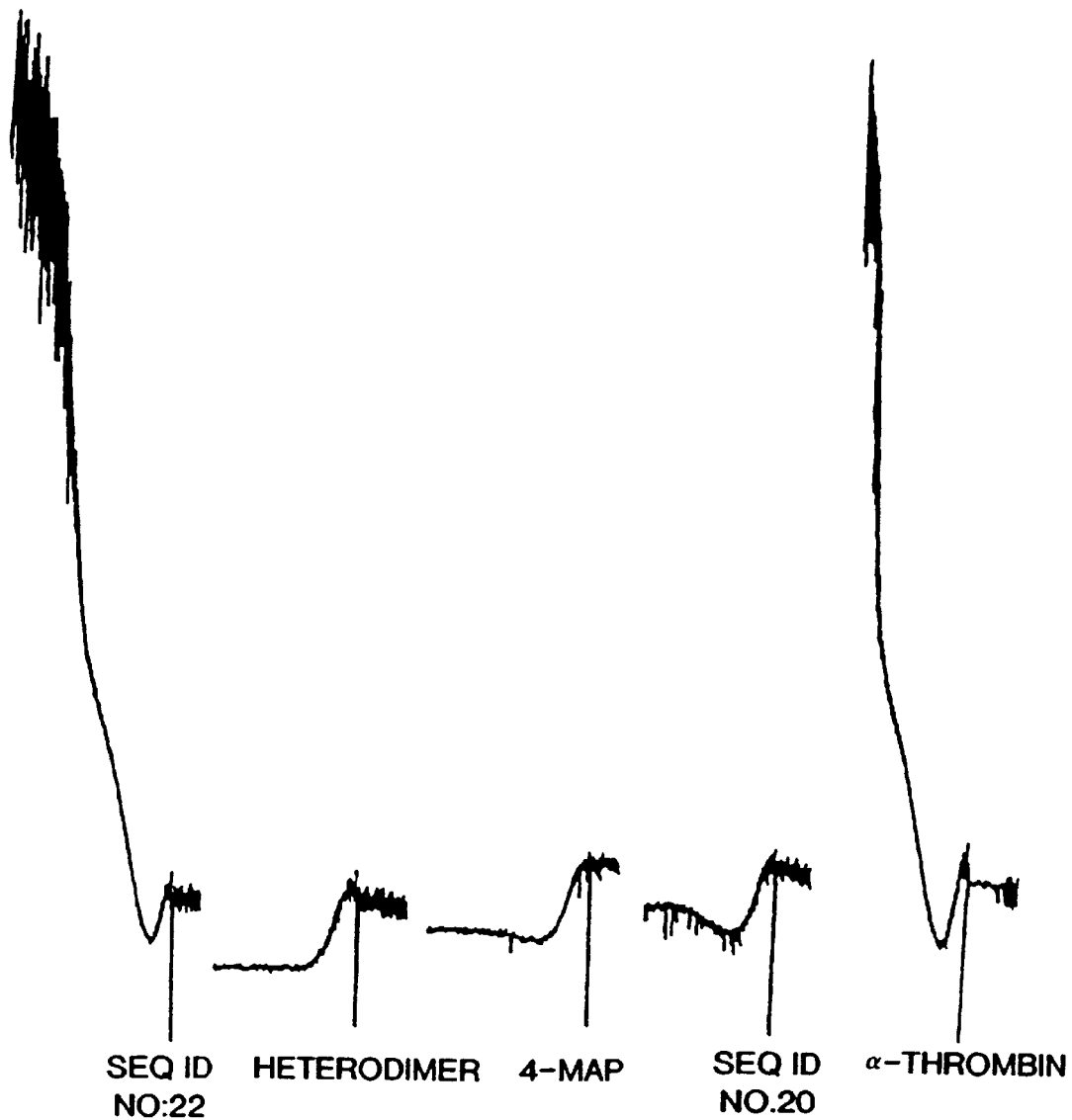

FIG. 11 shows the results of using a heterodimer BK analog (labeled "HETERODIMER") and 4-MAP on γ-thrombin-induced platelet activation. Human platelets in PRP were treated with 20 nM γ-thrombin. FIG. 11 shows the tracings from the aggregometer. When 1 mM BK analog SEQ ID NO:19, 0.05 mM 4-MAP, or 0.5 mM of the heterodimer was reacted with 20 nM γ-thrombin, the aggregation tracing was abolished. The specificity of this reaction was demonstrated by comparing the results to those for a reaction done with 1 mM of a non-BK analog peptide (SEQ ID NO:21). SEQ ID NO:21 was unable to alter the ability of γ-thrombin to induce platelet activation.

Taken together, the data from the rabbit and human platelet function inhibition studies, as well as the rabbit clearance study, demonstrate that the BK analogs described herein were able to inhibit thrombin-induced and ADP-induced platelet activation.

All references with respect to synthetic, preparative and analytic procedures are incorporated herein by reference.

The present invention may be embodied in other specific forms without departing from the spirit or essential attributes thereof and, accordingly, reference should be made to the appended claims, rather than to the foregoing specification, as indicating the scope of the invention.

What is claimed is:

1. A method of inhibiting thrombin-induced cell activation mediated by a thrombin receptor by inhibiting cleavage of the thrombin receptor on said cells comprising administering to an individual in need of such treatment an effective amount of a peptide, wherein said peptide has an amino acid sequence of the formula:

$$X_1\text{-Arg-Pro-Pro-Gly-}X_2$$

wherein:
$X_1$ is zero amino acids or the segment Gly-Met-Ile-Ser-Leu-Met-Lys (SEQ ID NO:23), or an N-terminal truncation fragment of said segment; and
$X_2$ is zero amino acids or the segment Phe-Ser-Pro-Phe-Arg-Ser-Ser-Arg-Ile (SEQ ID NO:24), or a C-terminal truncation fragment of said segment;
provided that the peptide is not native bradykinin.

2. A method according to claim 1 wherein the peptide comprises Arg-Pro-Pro-Gly-Phe (SEQ ID NO:19).

3. A method according to claim 2 wherein the peptide is Met-Ile-Ser-Leu-Met-Lys-Arg-Pro-Pro-Gly-Phe-Ser-Pro-Phe-Arg-Ser (SEQ ID NO: 12).

4. A method according to claim 2 wherein the peptide is Met-Lys-Arg-Pro-Pro-Gly-Phe-Ser-Pro-Phe-Arg-Ser-Ser (SEQ ID NO:13).

5. A method according to claim 2 wherein the peptide is Met-Lys-Arg-Pro-Pro-Gly-Phe-Ser-Pro-Phe-Arg-Ser-Ser-Arg-Ile-Gly (SEQ ID NO:14).

6. A method of inhibiting thrombin-induced cell activation mediated by a thrombin receptor comprising administering to an individual in need of such treatment an effective amount of a peptide, wherein the peptide has an amino acid sequence (D-Arg)-Arg-Pro-Hyp-Gly-Thi-Ser-(D-Tic)-Oic-Arg.

7. A method of inhibiting thrombin-induced cell activation mediated by a thrombin receptor by inhibiting cleavage of the thrombin receptor on said cells comprising administering to an individual in need of such treatment an effective amount of a peptide, wherein said peptide is comprised of one or more segments having the amino acid sequence $X_1$-Arg-Pro-Pro-Gly-$X_2$ and the peptide has the formula:

$$L\text{-}(X_1\text{-Arg-Pro-Pro-Gly-}X_2)_n$$

wherein:
L is a linker comprising a covalent bond or chemical group;
$X_1$, which may be the same or different in each segment, is zero amino acids or the sub-segment Gly-Met-Ile-Ser-Leu-Met-Lys (SEQ ID NO:23), or an N-terminal truncation fragment of said sub-segment;
$X_2$, which may be the same or different in each segment, is zero amino acids or the sub-segment Phe-Ser-Pro-Phe-Arg-Ser-Ser-Arg-Ile (SEQ ID NO:24), or a C-terminal truncation fragment of said sub-segment; and
n is an integer from two to twenty.

8. A method according to claim 7, wherein at least two of the segments are different.

9. A method according to claim 7, wherein the segments are identical.

10. A method according to claim 7 wherein n is two to four.

11. A method according to claim 7 wherein the segment is Arg-Pro-Pro-Gly-Phe (SEQ ID NO:19).

12. A method according to claim 7 wherein the peptide is:

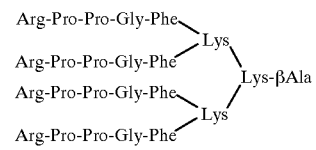

13. A method according to claim 7 wherein the peptide is:

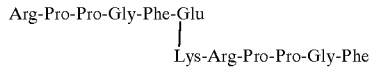

wherein the glutamic acid and lysine residues of said peptide are bonded through their respective side chains.

14. A method for preventing thrombin-induced platelet aggregation by inhibiting cleavage of a thrombin receptor on said platelets comprising administering to an individual in need of such treatment an effective amount of a peptide, wherein said peptide has an amino acid sequence of the formula:

$$X_1\text{-Arg-Pro-Pro-Gly-}X_2$$

wherein:
$X_1$ is zero amino acids or the segment Gly-Met-Ile-Ser-Leu-Met-Lys (SEQ ID NO:23), or an N-terminal truncation fragment of said segment; and
$X_2$ is zero amino acids or the segment Phe-Ser-Pro-Phe-Arg-Ser-Ser-Arg-Ile (SEQ ID NO:24), or a C-terminal truncation fragment of said segment;
provided that the peptide is not native bradykinin.

15. A method according to claim 14 wherein the peptide comprises Arg-Pro-Pro-Gly-Phe (SEQ ID NO:19).

16. A method for preventing thrombin-induced platelet aggregation by inhibiting cleavage of a thrombin receptor on said platelets comprising administering to an individual in need of such treatment an effective amount of a peptide, wherein said peptide is comprised of one or more segments having the amino acid sequence $X_1$-Arg-Pro-Pro-Gly-$X_2$ and the peptide has the formula:

L-(X₁-Arg-Pro-Pro-Gly-X₂)ₙ wherein:

L is a linker comprising a covalent bond or chemical group;

X₁, which may be the same or different in each segment, is zero amino acids or the sub-segment Gly-Met-Ile-Ser-Leu-Met-Lys (SEQ ID NO:23), or an N-terminal truncation fragment of said subsegment;

X₂, which may be the same or different in each segment, is zero amino acids or the sub-segment Phe-Ser-Pro-Phe-Arg-Ser-Ser-Arg-Ile (SEQ ID NO:24), or a C-terminal truncation fragment of said sub-segment; and n is an integer from two to twenty.

17. A method according to claim 16 wherein at least two of the segments are different.

18. A method according to claim 16 wherein the segments are identical.

19. A method according to claim 16 wherein n is two to four.

20. A method according to claim 16 wherein the segment is Arg-Pro-Pro-Gly-Phe (SEQ ID NO:19).

21. A method according to claim 16 wherein the peptide is:

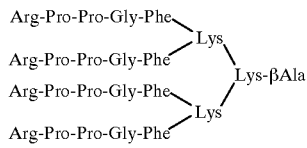

22. A method according to claim 16 wherein the peptide is:

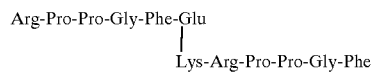

wherein the glutamic acid and lysine residues of said peptide are bonded through their respective side chains.

23. A compound having the formula:

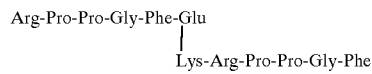

wherein the glutamic acid and lysine residues of said peptide are bonded through their respective side chains.

24. A pharmaceutical composition comprising a pharmaceutical carrier and a compound having the formula of claim 23.

25. A compound having the formula:

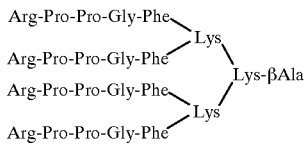

26. A pharmaceutical composition comprising a pharmaceutical carrier and a compound having the formula of claim 25.

27. The method of claim 2 wherein the peptide consists of Arg-Pro-Pro-Gly-Phe (SEQ ID NO:19).

28. The method of claim 15 wherein the peptide consists of Arg-Pro-Pro-Gly-Phe (SEQ ID NO:19).

29. A method for preventing platelet aggregation comprising administering to an individual in need of such treatment an effective amount of the peptide:

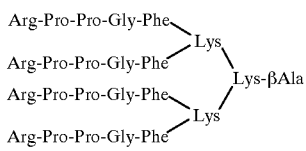

30. A method of inhibiting thrombin-induced cell activation mediated by a thrombin receptor comprising administering to an individual in need of such treatment an effective amount of a peptide selected from the group consisting of
Arg-Pro-Pro-Gly-Phe (SEQ ID NO:20);
Met-Ile-Ser-Leu-Met-Lys-Arg-Pro-Pro-Gly-Phe-Ser-Pro-Phe-Arg-Ser (SEQ ID NO:12);
Met-Lys-Arg-Pro-Pro-Gly-Phe-Ser-Pro-Phe-Arg-Ser-Ser (SEQ ID NO: 13); and
Met-Lys-Arg-Pro-Pro-Gly-Phe-Ser-Pro-Phe-Arg-Ser-Ser-Arg-Ile-Gly (SEQ ID NO:14).

31. A method of inhibiting thrombin-induced cell activation mediated by a thrombin receptor comprising administering to an individual in need of such treatment an effective amount of the peptide:

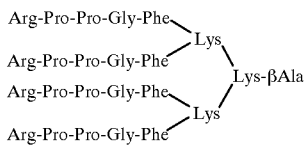

32. A method according to claim 15 wherein the peptide is selected from the group consisting of
Met-Ile-Ser-Leu-Met-Lys-Arg-Pro-Pro-Gly-Phe-Ser-Pro-Phe-Arg-Ser (SEQ ID NO:12);
Met-Lys-Arg-Pro-Pro-Gly-Phe-Ser-Pro-Phe-Arg-Ser-Ser (SEQ ID NO:13); and
Met-Lys-Arg-Pro-Pro-Gly-Phe-Ser-Pro-Phe-Arg-Ser-Ser-Arg-Ile-Gly (SEQ ID NO:14).

33. A method according to claim 6 wherein thrombin-induced activation of platelets is inhibited.

* * * * *